United States Patent [19]

Atweh

[11] Patent Number: 5,057,117
[45] Date of Patent: Oct. 15, 1991

[54] METHOD AND APPARATUS FOR HEMOSTASIS AND COMPARTMENTALIZATION OF A BLEEDING INTERNAL BODILY ORGAN

[75] Inventor: Nabil A. Atweh, Brooklyn, N.Y.

[73] Assignee: The Research Foundation of State University of New York, Albany, N.Y.

[21] Appl. No.: 344,970

[22] Filed: Apr. 27, 1989

[51] Int. Cl.$^5$ .......................... A61B 17/12; A61F 2/00
[52] U.S. Cl. .................................. 606/151; 606/202; 606/204; 600/37
[58] Field of Search ............... 606/151, 202, 203, 201, 606/204; 600/37; 128/87 R; 604/4

[56] References Cited

U.S. PATENT DOCUMENTS

| | | | |
|---|---|---|---|
| 3,091,242 | 5/1963 | Johnson, Jr. et al. | 128/402 |
| 3,186,404 | 6/1965 | Gardner | 128/DIG. 20 |
| 3,605,747 | 9/1971 | Pashkow | 128/303 |
| 4,039,039 | 8/1977 | Gottfried | 128/87 R |
| 4,066,084 | 1/1978 | Tillander | 606/202 |
| 4,217,890 | 8/1980 | Owens | 128/1 R |
| 4,370,754 | 2/1983 | Donzis | 2/2 |
| 4,399,809 | 8/1983 | Baro et al. | 606/202 X |
| 4,403,604 | 9/1983 | Wilkinson | 600/37 |
| 4,428,375 | 1/1984 | Ellman | 128/334 |
| 4,520,819 | 6/1985 | Birmingham et al. | 606/202 |
| 4,624,248 | 11/1986 | Poole et al. | 128/87 R X |
| 4,637,377 | 1/1987 | Loop | 600/37 |
| 4,674,479 | 6/1987 | Jennings et al. | 128/1 A |
| 4,885,811 | 12/1989 | Hayes | 128/870 X |

FOREIGN PATENT DOCUMENTS

| | | |
|---|---|---|
| 0141589 | 5/1985 | European Pat. Off. . |
| 2560518 | 3/1984 | France . |
| 1331002 | 9/1973 | United Kingdom . |
| 2178663A | 2/1987 | United Kingdom . |

OTHER PUBLICATIONS

Davol Rubber Company Catalogue, p. 24, 1959.
"Liver Packing for Uncontrolled Hemorrhage: A Reappraisal", by R. Ivatury et al., vol. 26, No. 8, The Journal of Trauma.
"Packing for Control of Hepatic Hemorrhage", by D. Feliciano et al., vol. 26, No. 8, The Journal of Trauma.
"The Use of Absorbable Mesh in Splenic Trauma", by D. Lange et al., vol. 28, No. 3, The Journal of Trauma.
"The Effects of Inflation of Antishock Trousers on Hemodynamics in Normovolemic Subjects", by T. Jennings et al., vol. 26, No. 6, The Journal of Trauma.
"Splenic Preservation with the Use of a Stapling Instrument: A Preliminary Communication", by B. Ravo et al., vol. 28, No. 1, The Journal of Trauma.

Primary Examiner—Robert A. Hafer
Assistant Examiner—Michael Brown
Attorney, Agent, or Firm—Hoffmann & Baron

[57] ABSTRACT

The present invention concerns methods and apparatus for compartmentalizing and carrying out hemostasis of a massively bleeding internal bodily organ of a patient. Generally, the apparatus includes a flexible compartment-defining structure having physical dimensions sufficient to generally conform to the gross geometry of a substantial portion of the organ. The flexible compartment-defining structure has an inner and outer surface, and is configurable so as surround and compartmentalize a substantial portion of the organ, with the inner surface facing the external surface of the organ. The apparatus of the present invention can be used to carry out hemostasis and/or the collection of blood for reprocessing and subsequent introduction to the patient by auto-transfusion. In another embodiment of the present invention, apparatus manipulates the surface-temperature of an internal bodily organ is also provided. Such apparatus further includes a flexible fluid-containable structure disposed over a substantial portion of the outer surface of the flexible compartment-defining structure, and is adapted for the passage of a gas or fluid therethrough in order to control the surface-temperature of the organ. In yet another embodiment of the present invention, a computer-graphic modelling and computer control system are provided in order to programmably control the surface-temperature and surface-pressure of the organ, while carrying out the methods of the present invention.

22 Claims, 14 Drawing Sheets

METHOD AND APPARATUS FOR HEMOSTASIS AND COMPARTMENTALIZATION OF A BLEEDING INTERNAL BODILY ORGAN

BACKGROUND OF THE INVENTION

1. Field of the Invention

The present invention relates generally to methods and apparatus for controlling bleeding from internal bodily organs, and/or manipulating the surface temperature or pressure thereof. More particularly, the present invention relates to method and apparatus carrying out hemostasis, retrieval of shedded blood, and other functions utilizing a device which surrounds the internal bodily organ.

In published reports by the National Center For Health Statistics, accidents including trauma, rank as leading cause of death in the age group 15-34 in the United States.

Trauma, blunt or penetrating, civilian or military, continues to be a major cause of bleeding and drainage of hospital and blood bank resources, with major loss of human life.

Solid abdominal organs are frequently injured by blunt and penetrating abdominal trauma. The peritoneal cavity does not provide adequate tamponade to stop bleeding from solid abdominal organs.

Several surgical techniques have been developed aiming at the control of bleeding from injured liver, spleen, kidney and other organs. These include suturing, resection and devascularization of the organ. A large number of liver, spleen and renal injuries do not respond to these techniques, leading to death of the patient or sacrifice of a valuable organ.

Major elective surgical procedures on the liver or other solid organs may also result in massive uncontrollable contributing to the high morbidity and mortality bleeding, associated with these procedures.

Known techniques for control of major bleeding from the liver include:

(1) suture ligation;
(2) surgical or radiographic devascularization,;
(3) resection; and
(4) packing of the peritoneal cavity.

Inspite of the above-mentioned techniques, mortality from major liver injuries remain very high and is associated with high morbidity related to massive transfusions, hypothermia and coagulopathy which contributes to the drainage of health care resources.

In two articles published in the Journal of Trauma, Volume 26, No. 8, 1986, entitled "Liver Packing For Uncontrolled Hemorrhage: A Reappraisal", by R. Ivatury, et al., and "Packing For Control Of Hepatic Hemorrhage", by D. Feliciano, et al., packing for massive liver bleeding has been described as a last resort when all other hemostatic techniques fail. However, such a method of hemostasis has numerous shortcomings and drawbacks. For example:

(1) the anatomy of the liver and other solid abdominal organs does not yield itself to adequate compartmentalization utilizing packing techniques;

(2) extensive amount of packs are needed leading to an increase in intra-abdominal pressure, and consequently, compromising the patient's ventilation;

(3) this technique is incapable of adequately saving shedded blood for the purpose of autotransfusion;

(4) this technique does not allow for the manipulation or otherwise control of the pressure applied to the bleeding organ during a process of attempting to achieve tamponade; and (5) the extensive foreign body effect relating to the liver packing of the peritoneal cavity leads to major septic complications.

Bleeding from the spleen, kidney, uterus and other organs can also lead to exsanguination. Several techniques have been applied to control bleeding from these organs. However, it is not infrequent that in desperation, sacrifice of the organ is undertaken to salvage the patient's life at a price of a major morbidity due to a loss of a valuable organ. In recent times, salvaging the spleen has become of major importance in the pediatric as well as the adult population since the medical community has learned more about the manifestations and consequences of post-splenectomy sepsis.

For the past two decades, attempts at splenic salvage have included:

(1) suturing techniques, which are occasionally successful;

(2) embolization of the splenic artery; and (3) wrapping the spleen with omentum and/or absorbable mesh material in the aim of tamponading the bleeding and/or covering the row surface that is bleeding.

However, like packing, prior art spleen wrapping techniques do not allow for controllable manipulation of pressure on the organ, provide a liquid seal around the organ, or allow for the monitoring, collection, processing and reinfusion of shedded blood, among other things.

In a similar fashion, trauma to the kidney or internal bleeding from the uterus as due to post partum complications and other pathological processes, may lead to the sacrifice of the organ, after the application of alternative techniques fail.

Accordingly, in view of the shortcomings and drawbacks of prior art methods and apparatus for achieving hemostasis in massively bleeding organs, there clearly is a great need for new methodologies and apparatus which improve the salvage of human lives and are capable of achieving such a function while decreasing morbidity and preserving much needed human blood and other hospital resources.

Therefore, it is a primary object of the present invention to provide a method and apparatus for compartmentalizing an organ, and having the potential capability of applying controlled pressure to achieve control of the bleeding from an organ such as the liver, spleen, kidney, uterus and other organs.

It is a primary object to the present invention to provide a method and apparatus aimed at controlling and/or collecting the blood shedded from a solid organ, from whatever cause, but most commonly due to trauma or surgery, for the purpose of monitoring and autotransfusion.

It is another object of the present invention to provide a novel method of managing frequently fatal clinical situations, and is expected to result in a decrease in the amount of blood transfusions needed to stabilize a traumatized internal bodily organ, and thus contribute to saving lives.

Another object is to provide a method and apparatus for carrying out hemostasis of a hemorrhaging bodily organ in which the method is performed in an operating room and enables a traumatized patient to be rapidly stabilized prior to being moved to another institution, with less danger of uncontrolled hemorrhage.

A further object of the present invention is to provide apparatus for achieving hemostasis of a hemorrhaging intra-abdominal organ, without compromising other organ functions, such as respiration, or applying (i.e. transmitting) pressure to other intra-abdominal or thoracic organs.

A further object of the present invention is to provide apparatus which can be easily fabricated as a self-contained disposable unit.

Another object of the present invention is to provide apparatus capable of manipulating the organ surfacetemperature.

Yet an even further object of the present invention is to provide apparatus for compartmentalizing an internal bodily organ and being capable of achieving other functions, while being easy to apply and remove from the body.

Other and further objects of the present invention will be explained hereinafter, and will be more particularly delineated in the dependent claims and other objects of the present invention will be apparent to those with ordinary skill in the art to which the present invention pertains.

SUMMARY OF INVENTION

The present invention concerns a method and apparatus for compartmentalizing an internal bodily organ. In general, the apparatus of the present invention comprises a flexible compartment-defining structure having physical dimensions sufficient to generally conform to the gross geometry of a substantial portion of the organ. The flexible compartment-defining structure has an inner and outer surface and is configurable so as to surround the compartmentalized portion of the organ, with the inner surface facing the external surface of the organ.

In one embodiment of the present invention, a flexible expandable receptacle means is disposed over a substantial portion of the inner surface of the flexible compartment-defining structure, and is positionable between the flexible compartment-defining structure and the organ. The flexible expandable receptacle means is capable of containing a volume of gas or liquid and expanding in response thereto, so as to expand and thereby apply a distribution of pressure to the external surface of the organ while a substantial portion of the organ is surrounded by and compartmentalized within the flexible compartment-defining structure, generally conforming to the gross geometry of the organ. Preferably, the flexible compartment-defining structure is made of a material which is impervious to blood, and includes a sealing means for bringing and sealing together the peripheral edges of the flexible compartment-defining structure, so as to form a compartment for surrounding a substantial portion of the organ, and having an opening for accommodating the extension of vital anatomical structures associated with the organ.

In one embodiment of the present invention, the compartment-defining structure of the apparatus hereof also includes at least one port formed therein, for the purpose of draining shedded blood which is collected within the compartment formed by the flexible compartment-defining structure surrounding the organ. The port includes a connection means for connecting a tube to the port, and in one embodiment, an auto-transfusion means is connected to the other end of the tube so that blood collected within the flexible compartment-defining structure is passed on to the auto-transfusion means for processing and subsequent reinfusion of the blood into the patient.

In one embodiment of the present invention, the flexible compartment-defining structure includes an outer flexible layer and an inner flexible layer which are joined together in order to form the flexible expandable receptacle means hereof. In particular, the outer flexible layer is made up of substantially non-elastic material which is impervious to gas and/or liquid, and has physical dimensions sufficient to generally conform to the gross geometry of the organ. The inner flexible layer is made of a material impervious to gas and/or liquid, and like the outer flexible layer, has physical dimensions sufficient to generally conform to the gross geometry of the organ. The inner flexible layer is hermetically sealed to the outer flexible layer, and overlaps adjacent portions thereof so as to form the flexible expandable receptacle means hereof. In such an embodiment, the inner flexible layer forms the inner surface of the flexible compartment-defining structure, whereas the outer flexible layer forms the outer surface of the flexible compartment-defining structure.

The hermetic sealing of the inner and outer flexible layers at overlapping adjacent portions, is preferably achieved in accordance with predetermined patterns and configurations in order to form the flexible expandable receptacle means. In one embodiment, the pattern configuration comprises a plurality of spaced-apart circles, all of which are enclosed by a boundary adjacent to the perimeter edges of the layers, and an expandable chamber is formed between a substantial portion of flexible layers which is capable of being filled with a volume of gas or liquid. The flexible expandable chamber is disposed over a substantial portion of the inner surface, and when filled with air or liquid, expands so as to apply a distribution of pressure to the external surface of the organ while partially surrounded by and compartmentalized in the flexible compartment-defining structure hereof.

In one embodiment of the present invention, a sealing means is also provided to the flexible compartment-defining structure for the purpose of bringing together and providing a liquid seal around the perimeter portions thereof, when the flexible compartment-defining structure is configured so as to surround and compartmentalize a substantial portion of the organ.

In one embodiment, the apparatus of the present invention further includes a supply of gas or liquid in fluid communication with the flexible expandable receptacle means. Alternatively, however, a pump and tubing can be used to fill the flexible expandable receptacle means with air in order to cause the flexible expandable receptacle means to expand and apply pressure to the external surface of the organ surrounded by the flexible compartment-defining structure.

Another aspect of the present invention is to provide apparatus for compartmentalizing an internal bodily organ, and therewhile to control the surface-temperature thereof in a controllable fashion. In such an embodiment, the outer surface of the flexible compartment-defining structure has a flexible fluid-containable receptacle means disposed over a substantial portion thereof, and is capable of containing a fluid or a gas, to be passed therethrough. In this embodiment, an organ surface-temperature supply and control means is provided, and includes a circulation means, and a supply of liquid or gas in fluid communication with the flexible fluid-containable receptacle means. The circulation means circulates the liquid or gas through the flexible fluid-containable receptacle means and a temperature control means is provided for controlling the temperature of the fluid or gas being circulated through the flexible fluid-containable receptacle means.

In order to monitor the surface-temperature of the organ, a plurality of surface temperature sensing means are disposed on the flexible compartment-defining structure. The organ surface-temperature control means is capable of programmably controlling the temperature of the gas or liquid in response to the surface-temperature of the organ, sensed by the surface-temperature sensing means. In order to monitor the surface-temperature of the organ, a monitoring means is provided, and a display means is also provided for displaying the surface-temperatures thereon.

Another aspect of the present invention concerns a work station for use in conjunction with the above-described apparatus hereof. The work station has the capability of modelling in real-time, the organ which is compartmentalized within the flexible compartment-defining structure hereof, and displaying the same on a visual display monitor, along with detected organ surface-pressures, organ surface-temperatures and monitored shedded blood flow rates as well.

control interface is provided to the work station so A user that a health professional can programmably control and monitor, from the work station the organ surface-temperature, surface-pressure, and shedded blood flow rates.

Using the apparatus of the present invention, one or more functions can be carried out by compartmentalizing the internal bodily organ of the patient which is massively bleeding, according to the principals of the present invention.

In particular, the present invention provides a method of carrying out hemostasis and blood collection simultaneously using for example, the apparatus of the present invention. The present invention also provides a method of controlling the surface-temperature of a solid organ using another embodiment of the apparatus hereof.

As a result of the present invention, the shortcomings and drawbacks of the prior art methodologies have been overcome, and a significant contribution to the surgical arts has been made.

BRIEF DESCRIPTION OF THE DRAWINGS

For a full understanding of the objects of the present invention, reference is made to the following detailed description of the preferred embodiments which is to be taken in connection with the accompanying drawings, wherein.

DETAILED DESCRIPTION OF THE PREFERRED EMBODIMENTS OF THE PRESENT INVENTION

Referring to FIGS. 5A, 5B, 5C, 6A, 6B, 7A, 7B, 8A and 8B, in particular, the detailed description of the compartment-defining apparatus of the present invention for surrounding an internal bodily organ, will be given below as follows.

In general, the apparatus of the present invention comprises a flexible compartment-defining structure 1 having physical dimensions sufficient to generally conform to the gross geometry of a substantial portion of an organ. Notably, in the embodiments illustrated in FIGS. 5A, 5B, 5C, 6A, 6B, 7A, 7B, 8A and 8B, as herein disclosed, the organ is a liver of a human patient, however, apparatus constructed in accordance with the principles of the present invention, is intended for use in connection with other organs as well, including the spleen, kidney, and uterus. These other embodiments of the present invention are illustrated in FIGS. 10A, 10B, 11A, 11B, 12A, and 12B, respectively, and will be described hereinlater.

While the flexible compartment-defining structure 1 may be constructed using a variety of construction techniques, there are however, structural requirements that should be satisfied in order to carry out the methods of the present invention, as will be described hereinafter.

One such structural requirement is that the flexible compartment-defining structure 1 be in fact (i) flexible, (ii) have an inner and outer surface, and (iii) be configurable so as to surround and compartmentalize a substantial portion of a traumatized organ so that the inner surface thereof, faces the external surface of the organ.

Figure 5A:
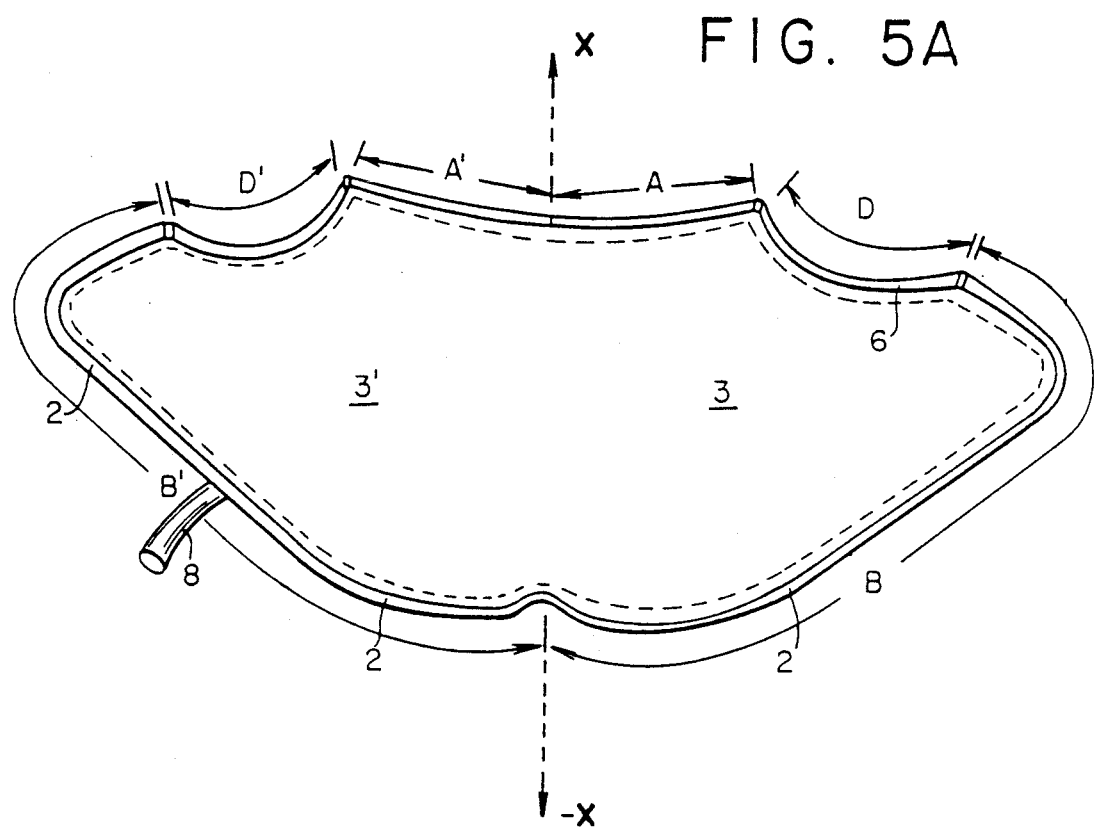
FIG. 5A is a plan view of one embodiment of the apparatus of the present invention for surrounding and compartmentalizing a substantial portion of the liver, shown in an unassembled state to illustrate its hermetically-sealed double-wall construction.
Figure 5B:
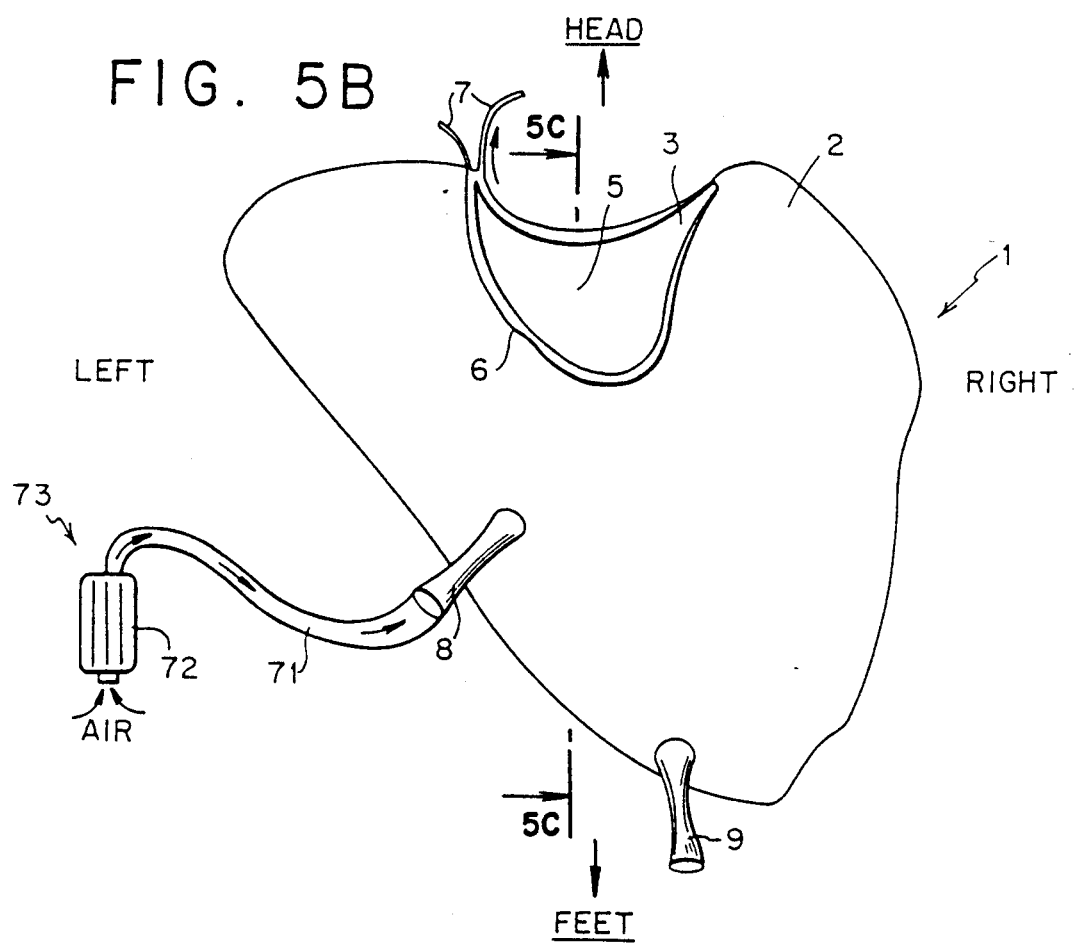
FIG. 5B is a perspective posterior view of the apparatus illustrated in FIG. 5A, shown fully assembled.

In FIG. 5B, one embodiment of the apparatus for surrounding an internal bodily organ such as the liver of a patient, is shown in the form of a jacket-like assembly 1 comprising outer flexible layer 2 and an inner flexible layer 3 joined together in a manner described in FIG. 5A.

The outer flexible layer 2 is made of a substantially non-elastic material which is impervious to gas or liquid, and most particularly, impervious to blood, and has physical dimensions sufficient to generally conform to the gross geometry of the liver (not shown). The inner flexible layer 3 is made of a material impervious to gas or liquid, particularly shedded blood, and has also physical dimensions sufficient to generally conform to the gross geometry of the liver.

Figure 5C:
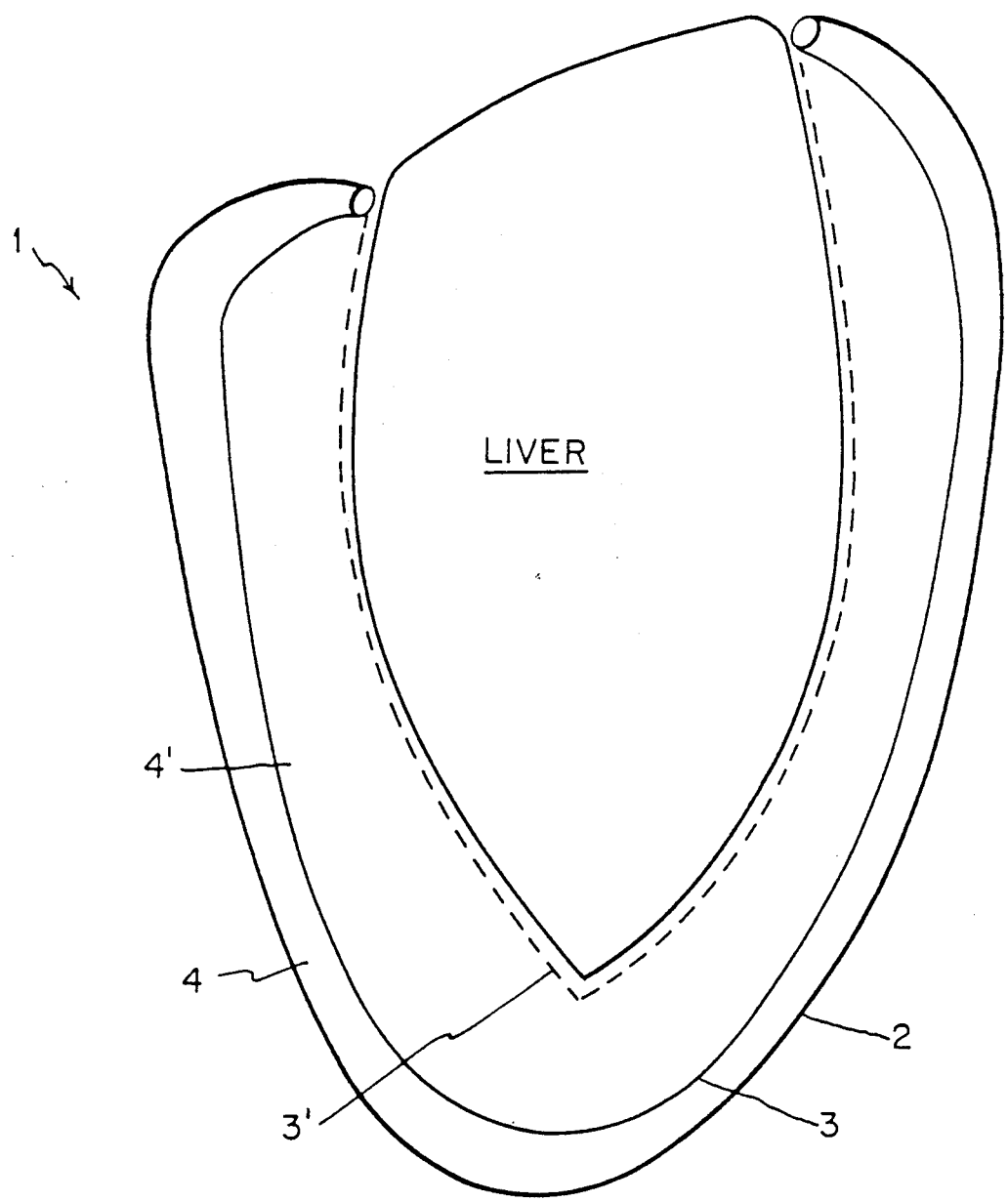
FIG. 5C is a cross-sectional view of the apparatus shown in FIG. 5B, taken along line 5C–5C with a cross-sectional representation of the liver shown interposed and compartmentalized within the volumetric-space defined by the inner walls of the compartment-defining structure hereof.

Referring to FIGS. 5A and 5C in particular, the inner flexible layer 3 is hermetically sealed (along broken lines) to the outer flexible layer 2 at overlapping adjacent perimeter edge portions thereof, so as to form a flexible expandable receptacle means 4. Notably, in this embodiment the flexible expandable receptacle means 4 is realized as the flexible expandable chamber, or bladder, formed between the two flexible layers 2 and 3 as clearly illustrated in FIG. 5C. After the flexible expandable chamber 4 is formed, the double-walled chamber in the compartment-defining structure 1 with expandable chamber 4 realized therein, is folded upon itself about the x-axis shown in FIG. 5A, and corresponding points along the perimeter edges A' and A and B' and B are brought and sealed together so as to form the "jacket-like" compartment-defining structure 1 illustrated in FIG. 5B.

While the embodiment shown in FIGS. 5A, 5B and 5C has realized as a flexible bladder or chamber 4 formed between the inner and outer flexible layers 2 and 3, respectively, this flexible bladder or chamber 4 shall be referred to hereinafter and especially in the claims, as the flexible expandable receptacle means hereof.

Notably, with such construction, the inner flexible layer 3 of the flexible compartment-defining structure 1 is formed from the inner surface thereof, whereas the outer flexible layer 2 of the compartment defining structure 1 is formed from the outer surface thereof.

The flexible expandable chamber 4 is disposed over a substantial portion of the inner surface and is positionable between the flexible compartment-defining structure 1 and the organ. The flexible expandable chamber 4 is capable of containing a volume of gas or liquid under pressure, for applying a distribution of pressure to the external surface of the liver, while a substantial portion of the organ is surrounded by and compartmentalized within the flexible compartment-defining structure 1, generally conforming to the gross geometry of the liver.

As shown in FIGS. 5B, apparatus 1 of the present invention includes an opening 5 formed in the flexible compartment-defining structure 1. The opening 5 in apparatus of FIG. 5B provides an opening through which a mobilized liver can be inserted into the expandable three-dimensional volume (i.e. compartment) defined by the flexible compartment-defining structure 1 of the present invention. As will be described in greater detail hereinafter, the portal triad of the liver and inferior vena cava is allowed to extend from opening 5 when the compartment-defining structure surrounds and compartmentalizes a substantial portion of the liver. In order to reduce the size of the opening 5, the embodiment in FIGS. 5A and 5B is provided with a "purse string" type closing device formed by a fine sleeve formed at the perimeter defining edges D' and D of opening 5, through which a purse string 7 or functionally like structure is weaved therethrough, to create a purse string-like mechanism. Upon applying the apparatus 1 of the present invention about a traumatized liver, with the portal triad and inferior vena cava extending from the opening 5, the purse string 7 can then be pulled so as to reduce the opening 5, so that the compartment-defining structure 1 snugly fits about the organ, as desired.

In order that the flexible expandable chamber 4 of the jacket-like structure 1 is fillable with a volume of gas or liquid as discussed above, a air/gas input port 8 is formed in the outer flexible layer 2 of the compartment-defining structure 1. By attachment of a supply of gas or liquid 73 placed outside the body to the gas/liquid port 8 as illustrated in FIG. 5B, the chamber 4 defined between the outer and inner flexible layers 2 and 3, can be filled with gas or liquid so that the inner flexible layer 3 expands inwardly towards the liver. In FIG. 5C, the function of the flexible expandable chamber 4 is clearly illustrated. For example, when the volume of gas or liquid is introduced into chamber 4, the inner flexible layer 3 expands inwardly toward the "Liver" so as to apply a distribution of pressure to the surface thereof. In this expanded volumetric state, the expanded flexible chamber 4 is denoted by 4' and the flexible inner layer is denoted by 3'.

In order that the apparatus shown in FIGS. 5A and 5B is capable of draining shedded blood collected within the compartment or space defined by the flexible compartment-defining structure 1, a blood drainage port 9 is formed through the outer flexible layer 2 and inner flexible layer 3 of the compartment-defining structure 1 so as to be in fluid communication with the volumetric-space defined by the inner surface of the flexible layer 3. As will be discussed hereinafter, shedded blood collected within from the
tus 1 of the present invention can be provided to appara autotransfusion apparatus located outside the body for processing and subsequent reinfusion to the patient.

Figure 6A:
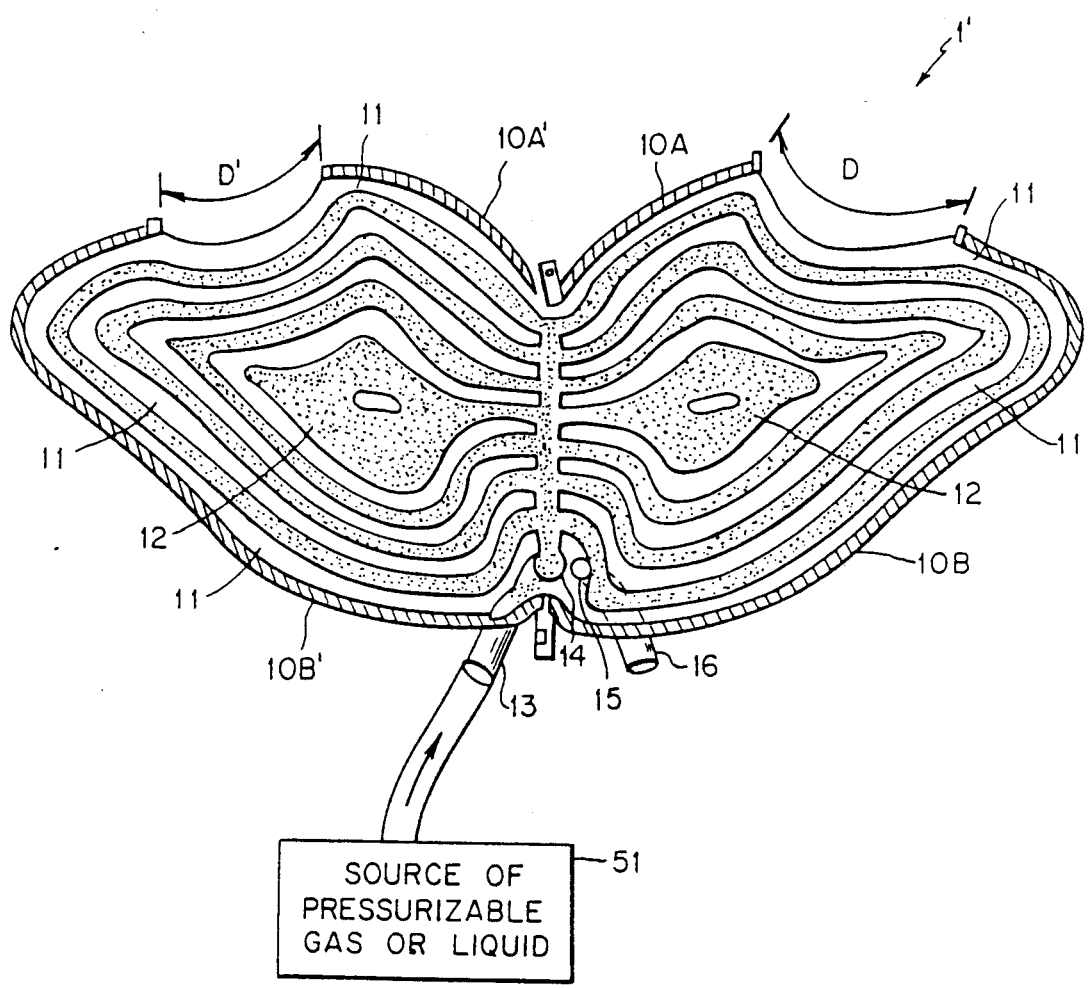
FIG. 6A is a plan view of a second embodiment of the apparatus of the present invention, showing the flexible compartment-defining layer disposed substantially in two-dimensions and having dimensions sufficient to generally conform to the gross geometry of a substantial portion of the liver, with the flexible expandable receptacle means disposed over a substantial portion of the inner surface.
Figure 6B:
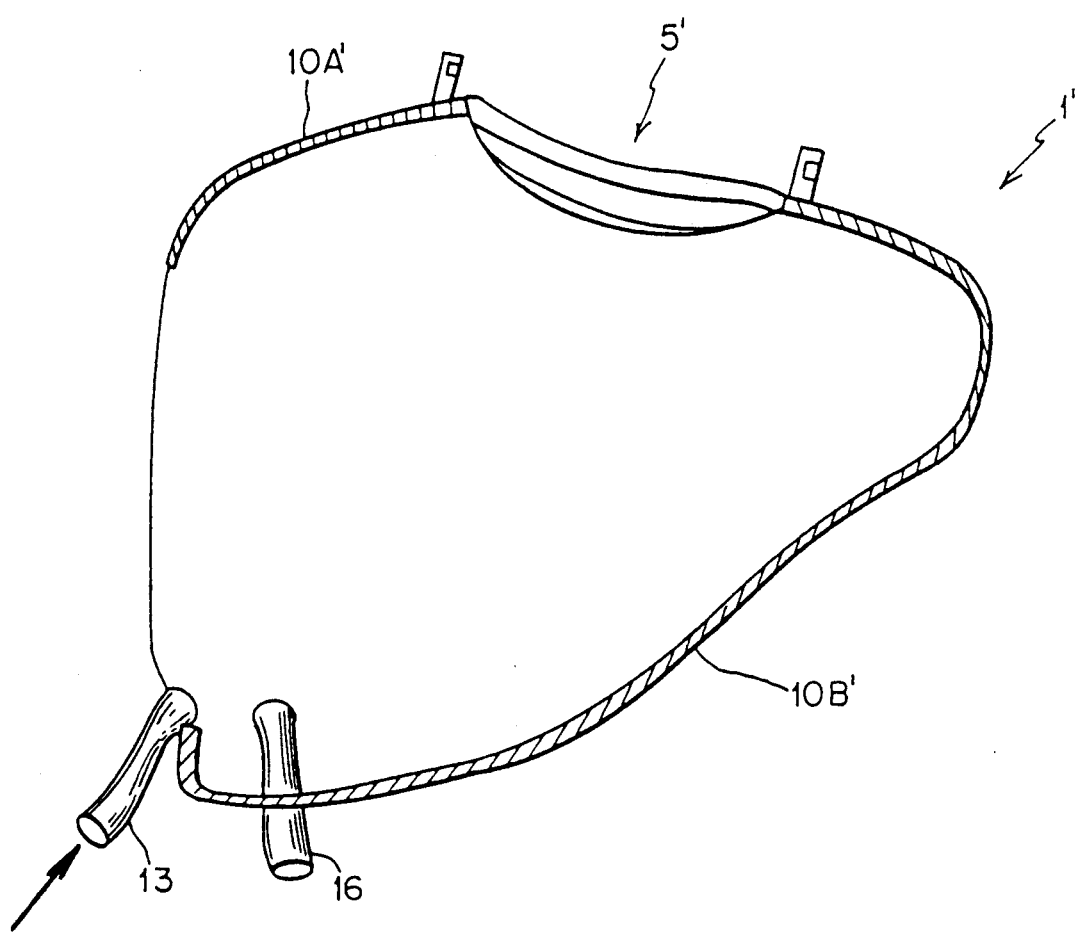
FIG. 6B is a perspective view of the apparatus shown in FIG. 6A, in which the flexible compartment-defining structure thereof is configured and a portion of its perimeter edges brought and sealed together so as to enclose a three-dimensional space within which a liver can be surrounded and compartmentalized within the peritoneal cavity.

Referring now to FIGS. 6A and 6B, an alternative embodiment of apparatus for compartmentalizing an internal bodily organ of a patient, is shown.

In FIG. 6A, in particular, a compartment-defining structure 1' for compartmentalizing a liver is shown in plan view with compartment-defining structure including a pair of zipper members 10A' and 10A and 10B' and 10B, provided to the perimeter edges of the compartment-defining structure 1', and shown disposed in their unzippered "open" state. These zipper members function as sealing means for bringing together and providing a liquid seal to the perimeter edge portions when the compartment-defining structure 1' is configured so as to surround and compartmentalize a substantial portion of the organ. As illustrated in FIGS. 6A and 6B, the compartment-defining structure 1' has physical dimensions sufficient to generally conform to the gross geometry of a substantial portion of the liver, i.e. when the zipper members 10A'/10A and 10B'/10B are zippered up, as shown in FIG. 6B. The principal requirement of such zipper members are that they provide a blood-tight seal, and do not pinch or cut the external surface of the organs.

Along the perimeter edges of the compartment-defining structure 1' shown in FIG. 6A, there are portions D' and D of the perimeter edges which are not provided with zipper members, in order to form an opening 5' when the zippers are zippered up and the compartment-defining structure is configured so as to surround and compartmentalize the liver as shown in FIG. 6B.

As illustrated in FIG. 6A, on the inside surface 11 of the open compartment-defining structure 1', there is provided a flexible expandable receptacle means realized in the preferred embodiment, in the form of a symmetrically patterned arrangement 12 (i.e. expandable bladder or chamber) comprising a network of expandable chambers, the resultant geometry of which appears similar to the lines on a butterfly's wing. This network of flexible expandable chambers 12 has one input port 13 formed on the outside of the flexible compartment-defining structure 1' and feeds the network of chambers with either a fluid (i.e. a liquid or gas) supplied under pressure, in order to cause the flexible expandable chambers 12 to expand when the compartment-defining structure 1' is configured to surround the liver. As a result of the expansion, a distribution of pressure is applied to the external surface of the liver, in order to achieve hemostasis thereof. As with the embodiment illustrated in FIGS. 5A, 5B and 5C, this particular embodiment also has an "output-port" since the flexible expandable chamber 12 is a closed circuit of air/liquid bladders, which is necessary to achieve expansion upon the introduction of a volume of liquid or gas into the network of expandable chambers.

The configuration of flexible expandable chambers 12 shown in 6A, is symmetric in order.to produce a predetermined pressure pattern upon the external surface of the liver. However, the configuration of the flexible expandable receptacle means 12 hereof, can vary in shape and geometry without departing from the scope and spirit of the present invention.

The construction of the embodiment shown in FIGS. 6A and 6B, differs in several ways from the embodiment shown in FIGS. 5A, 5B and 5C. In particular, the apparatus shown in FIGS. 6A and 6B does not comprise an inner and outer layer per se, but rather has an outer flexible layer 11 made of a substantially non-elastic material impervious to gas or liquid. Such a material can be for example, reinforced Silastic R brand material, however, other functionally equivalent materials, for example, having biodegradable , can expectedly be used as well. properties To form the flexible expandable chamber 12 (i.e. the flexible expandable receptacle means hereof) disposed on the inside surface of flexible layer 11 shown in FIG. 6A, one of several possible techniques can expectedly be used. For example, a network of preformed expandable inflatable chambers having the geometry shown in FIGS. 6A, can be attached to the inside of flexible layer 11, using an adhesive, ultrasonic welding or heat stamp welding, all known in the art. With a hole 14 formed in the flexible layer 11, input port 13 can be attached to an access opening of the flexible expandable chamber network 12.

As illustrated in FIG. 6B, when the flexible compartment defining structure is applied about a mobilized liver by surrounding the same and zippering up the sealing members 10A'/10A and 10B'/10B, then a "blood-tight" compartment is formed about the liver as desired. Thus, upon introduction of a volume of gas or liquid at the input port 13, the flexible expandable chamber 12 expands and thereby applies a predetermined distribution of pressure to the external surface of the liver, to achieve hemostasis. Notably, as in the embodiment of FIGS. 6A and 6B, a shedded-blood drain port 16 can be provided through a hole 15 formed in one or more of the walls of the compartment-defining structure 1' for draining shedded blood collected therein, and passing the same through the abdominal wall to an autotransfusion or like device positioned outside the body for the purposes of further collecting and processing of shedded blood from the liver, and subsequent reinfusion into the patient.

While the embodiments of FIGS. 6A and 6B include the use of zipper members 10A'/10A and 10B'/10B which seal together the perimeter edges of the flexible compartment-defining structure of the present invention, functionally equivalent sealing means can expectedly be used as well. However, regardless of whether or not plastic zipper members or other fastening and sealing means are used for this purpose, a blood-tight seal should be formed at the perimeter edges of the compartment-defining structure, so that shedded blood from the traumatized organ can be adequately collected as desired, while hemostasis is being carried out by the introduction of pressurized air or liquid to the network of flexible expandable chamber 12.

Figure 7A:
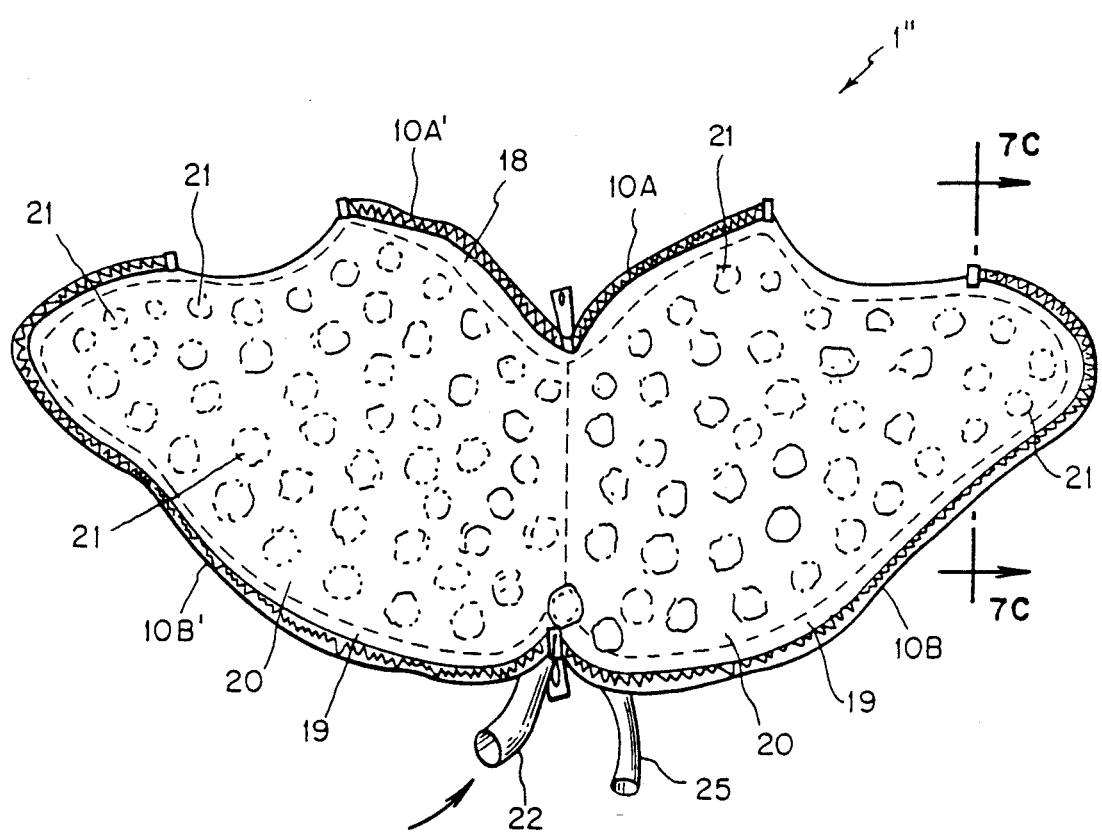
FIG. 7A is a plan view of a third embodiment of the apparatus of the present invention, showing the flexible compartment-defining structure disposed substantially in two-dimensions and having physical dimensions sufficient to generally conform to the gross geometry of a substantial portion of the liver, with the flexible expandable receptacles disposed over a substantial portion of the inner surface.
Figure 7B:
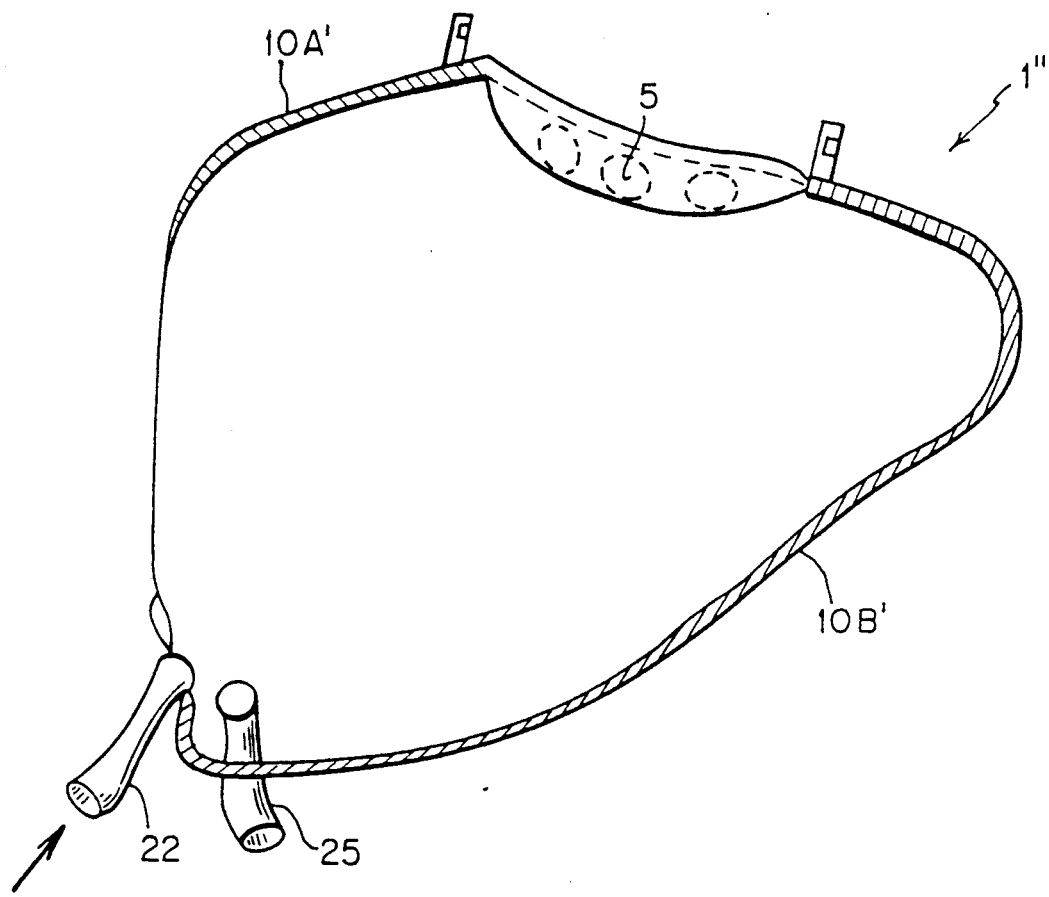
FIG. 7B is a perspective view of the apparatus shown in FIG. 7A, in which the flexible compartment-defining structure thereof is configured and a portion of its perimeter edges brought sealingly together so as to enclose a three-dimensional space within which a liver can be partially surrounded and compartmentalized within the peritoneal cavity.
Figure 7C:
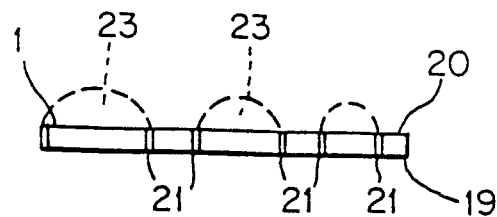
FIG. 7C is a cross-sectional view of FIG. 7B taken along line 7C–7C.

Referring now to FIGS. 7A, 7B and 7C in particular, another embodiment of the apparatus of the present invention is shown. In FIG. 7A, the flexible compartment-defining structure 1''' has disposed on its inner surface 18, the flexible expandable receptacle means hereof realized in the form of a continuous, flexible and expandable chamber formed over a substantial portion of the inner surface 18 of structure 1''. Over the inner surface 18 of the compartment-defining structure 1'', a plurality of spaced-apart circular zones are formed, which are not fillable with air or liquid in order to produce a "button-in-a-pillow effect". This particular feature is particularly advantageous in that it provides channels for the free flow of shedded blood between the external surface of the organ and inner surface of apparatus 1'', to drain and subsequently be collected for autotransfusion.

One manner in which this embodiment of the flexible expandable receptacle means hereof is formed, is by applying a flexible expandable resilient layer of material 20 over the flexible non-expandable outer layer 19 of the compartment-defining structure 1'', and to hermetically seal the flexible expandable layer 20 to the non-expandable layer 19, at locations indicated by dotted lines shown in FIG. 7A. Notably, these locations are along the perimeter outlines of the circular patterns 21 and the flexible compartment-defining structure 1''. This hermetic sealing operation results in the formation of a continuous flexible gas/liquid chamber 23 illustrated in FIG. 7C. This chamber is fillable from an input port 22 which has fluid access to the interior of the flexible expandable chamber 23 through the rear portion of the flexible compartment-defining structure 1'', similar to the embodiment disclosed in FIG. 6A and 6B.

As a volume of gas or liquid is provided to the input port 22, the space 4 between the inner flexible expandable layer 20 and the outer flexible non-expandable layer 19, fills with air or liquid (as the case may be) and causes the flexible expandable inner layer 20 to expand as illustrated in FIG. 7C. This expansion, in turn, causes a decrease in the volume formed between the inner and outer surfaces of the compartment-defining structure, i.e. when configured so as to surround and compartmentalize a liver as shown in FIG. 7B. Consequently, the expansion of the flexible expandable chamber 23 causes a pressure distribution to be applied to the traumatized organ compartmentalized within compartment-defining structure 1'', so as to achieve hemostasis thereof in a manner which will be discussed in greater detail herein below. In order to collect shedded blood, blood drainage port 25 is provided in a manner described in the embodiment of FIGS. 7A and 7B.

Figure 8A:
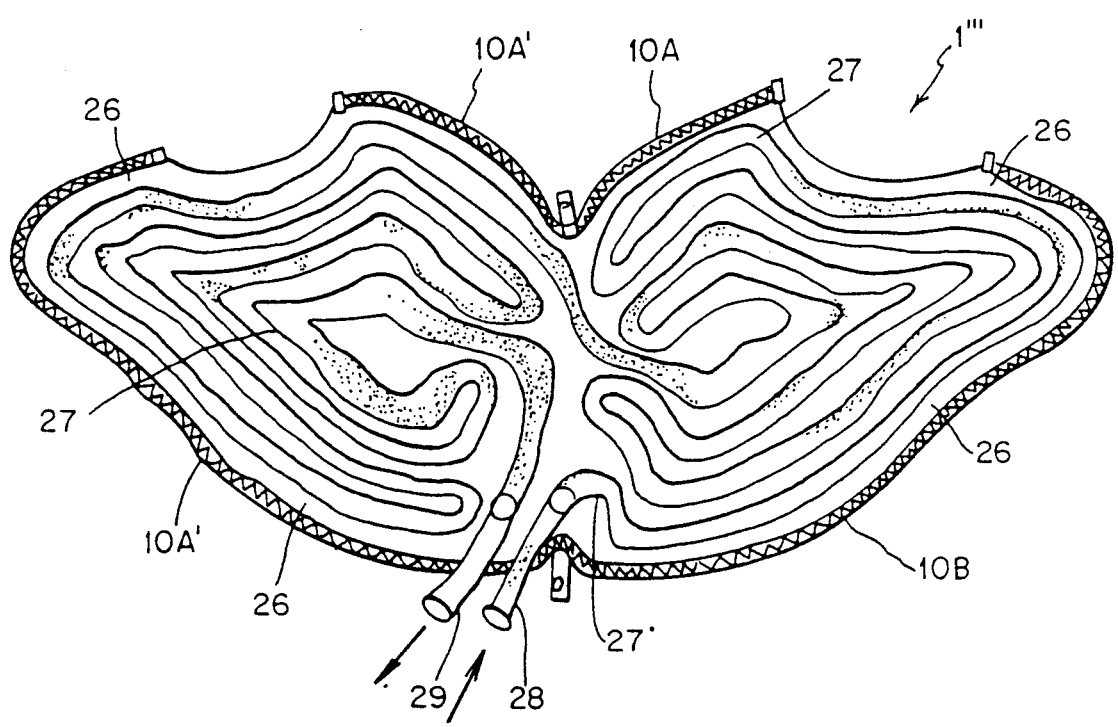
FIG. 8A is a plan view of a fourth embodiment of the apparatus of the present invention, showing the flexible compartment-defining structure disposed substantially in two-dimensionals and having physical dimensions sufficient to generally conform to the gross geometry of a substantial portion of the liver, with the flexible fluid-containable structures disposed over a substantial portion of the outer surface of the compartment-defining structures.
Figure 8B:
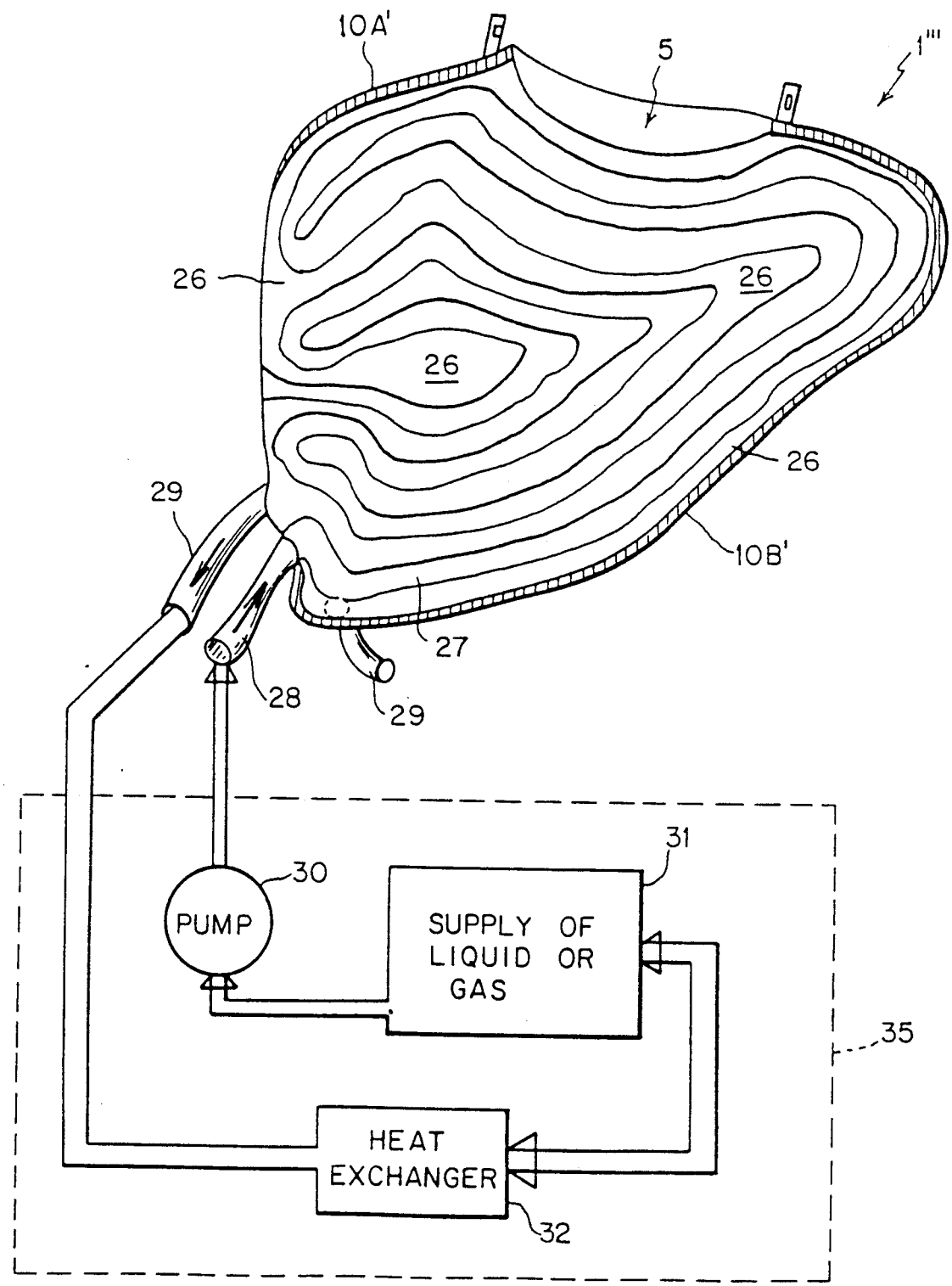
FIG. 8B is a perspective view of the apparatus shown in FIG. 8A, in which the flexible compartment-defining structure thereof is configured and a portion of its perimeter edges brought together so as t oenclose a three-dimensional space within which a liver can be surrounded and compartmentalized within the peritoneal cavity.

Referring now to FIGS. 8A and 8B, another embodiment of the apparatus for containing a traumatized liver, is shown. In FIG. 8, the outer surface of the flexible compartment-defining structure 1''' is shown disposed in two dimensions, with zipper members 10A'/10A and 10B'/10B engaged in their "open" state. Notably, the overall geometry of the flexible compartment-defining structure 1''' is substantially similar to the embodiments illustrated in FIGS. 5A/5B, 6A/6B and 7A/7B. On the outside surface 26 of the flexible compartment-defining structure 1''', a flexible fluid-containable receptacle means is disposed over a substantial portion thereof and is capable of containing a volume of liquid or gas to be passed or otherwise circulated therethrough, for heat exchange purposes to be discussed is er detail hereinbelow. great As shown in the embodiment of FIGS. 8A and 8B, the flexible fluid-containable receptacle means hereof is realized in the form of a gas/fluid-carrying tubular network 27 having an input port 28 and an output port 29 for the introduction and removal of a liquid or a gas, respectively. Between the input and the output ports 28 and 29 respectively, a liquid or gas can be passed through the tubular network 27 so as to transfer heat away from (or to) an organ which is being surrounded by the compartment-defining structure 1''' bearing the flexible tubular network 27 on its outer surface 26, as shown in FIG. 8B. In addition, a blood drainage port 29 can also be provided to the flexible compartment-defining structure 1''' for the collection of shedded blood from the traumatized organ during a surgical procedure, utilizing the apparatus shown in FIG. 8A.

As illustrated in FIG. 8B, a fluid circulation means, such as a pump 30, is provided to a circuit comprising a supply of liquid or gas 31 connected in fluid communication with the flexible expandable tubular network 27. The pump 30 provides for the circulation of the liquid or gas through the flexible tubular network 27 in order to achieve heat exchange between the liquid or gas and the organ. To maintain the temperature of gas or liquid, a temperature control means 32, e.g. heat exchanger, is connected within the fluid circuit of FIG. 8B.

As is apparent from FIG. 8B, a liver surrounded by and compartmentalized within the flexible compartment-defining structure 1''', bearing the flexible fluid-containable tubular network 27, is most suitable for manipulating the temperature of a traumatized organ during a particular surgical procedure or during organ procurement and implantation. A method of using such apparatus shown in FIGS. 8A and 8B, will be discussed in greater detail hereinbelow.

Figure 9:
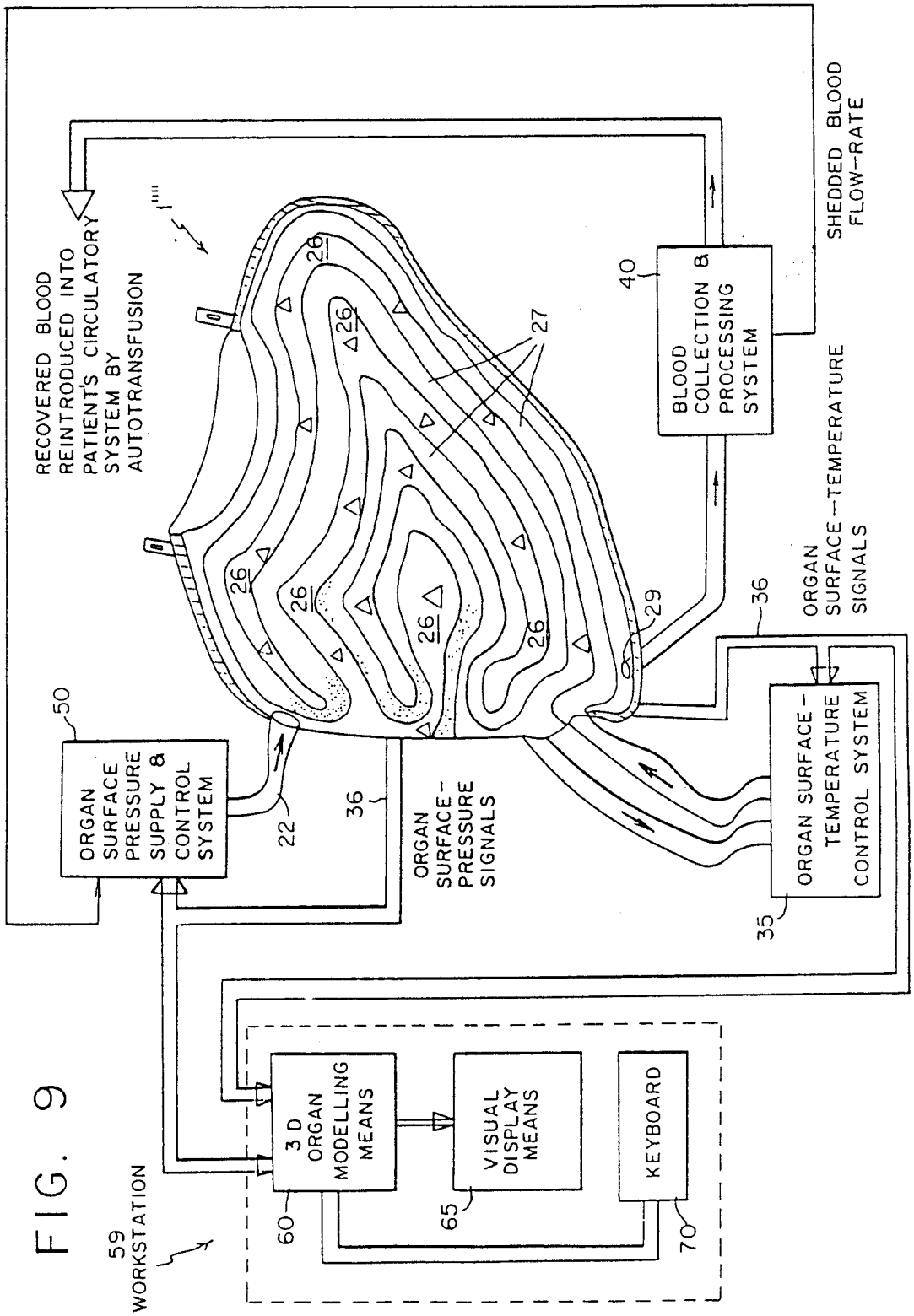
FIG. 9 is a block function system diagram of yet another embodiment of the present invention, in which compartmentalization of an internal bodily organ can be carried out under controllably monitored organ surface pressure conditions while recovering shedded blood from the bleeding organ for auto transfusion, in addition to providing organ surface-temperature monitoring and control, and three-dimensional computer modelling of the organ and the real-time visual display thereof along with measurements of monitored organ surface-pressure, organ surface-temperature, and flow-rates of collected shedded blood.

Turning now to FIG. 9, a preferred embodiment of the apparatus of the present invention is shown, in which all of the features of the present invention illustrated in FIGS. 5A, 5B, 6A, 6B, 7A, 7B, 8A and 8B are integrated into one system capable of carrying out several functions.

In FIG. 9, yet another embodiment of the flexible compartment-defining structure 1'''' is shown, configured so as to surround and compartmentalize a traumatized liver (not shown). This embodiment of the flexible compartment-defining structure hereof incorporates the inventive features of the embodiments disclosed in FIGS. 5A/5B, 6A/6B, 7A/7B, and FIG. 8A/8B. Specifically, the flexible compartment-defining structure 1''' has disposed over a substantial portion of its inner surface, the flexible expandable receptacle means hereof (not shown) which can be any one of the embodiments illustrated in FIGS. 5A/5B, 6A/6B or 7A/7B. On the outer surface of the flexible compartment-defining structure 1'''', there is disposed the flexible fluid-containable receptacle means (i.e. tubular network) of the form illustrated in FIGS. 8A and 8B, for example.

The input and output ports 28 and 29 respectively of this embodiment of apparatus for organ compartmentalization, are connected to respective ports of an organ surface-temperature control system 35. In general, the organ surface-temperature control system 35 comprises: the supply of liquid or gas 31 connected in fluid communication with the flexible fluid-containable receptacle means (i.e. flexible tubular network) 27; the pump 30 for circulating the liquid or gas through the flexible tubular network 27; and the temperature control means 32 for controlling the temperature of the fluid or gas being circulated through the flexible tubular network 27. In one embodiment of the present invention, the fluid to be passed through the flexible tubular network 27 is a non-toxic heat exchanging liquid or gas.

In order to detect the organ surface-temperature at various locations on the organ, a network of spaced-apart temperature sensors (indicated by triangles Δ on surface 26) are mounted through the walls of the flexible compartment-defining structure 1''', for example, between the tubular passage ways 27, and within the hermetically sealed circular patches 21 as shown in FIG. 7A. The temperature-sensors can be realized as heat-sensitive crystal devices installed through the walls at 21, in a liquid-tight manner. Each sensor is connected to appropriate instrumentation circuitry (not shown), known in the art. The temperature-sensors serve the function of detecting a plurality of organ surface-temperature values 36, which are converted in numerical form for monitoring purposes, in a manner known in the biomedical instrumentation arts.

In order to collect shedded blood from the traumatized organ during, for example, a surgical operation, the blood drainage port 29 formed through the compartment-defining structure 1''', is maintained in fluid communication with a blood collection and processing system 40, also known in the art for collecting and processing blood for reintroduction to the patient's circulatory system, by principles of autotransfusion.

In order to carry out hemostasis of a traumatized organ which is massively bleeding, the input port 22 of the flexible expandable chamber 27 is connected in fluid-communication with an organ surface-pressure supply and control system 50 as illustrated in FIG. 9. The organ surface-pressure supply and control system 50 typically includes a supply of gas or liquid 51 as in FIG. 6A for introduction under pressure into the expandable chambers of the expandable receptacle means 27 hereof. However, in order to maintain a constant supply of pressure, a pump or functionally equivalent means (e.g. hand-squeezable air-bulb and tubing 73 as illustrated in 5B) can alternatively be provided for introducing gas or liquid into the flexible expandable receptacle means hereof, and maintaining the introduced volume of gas or liquid at a predetermined pressure.

In order to determine an appropriate level of pressure for carrying out hemostasis, (i.e. a stoppage of shedded blood from a traumatized organ), the shedded blood collected from the compartment-defining structure 1'''' is monitored by the blood collection and processing system 40. On the basis of the monitored shedded blood flow rate and the organ surface-pressure signals, the amount of pressure necessary to achieve the hemostasis is determined. In order to produce such organ surface-pressure signals, pressure transducers are provided to the surfaces of the expandable chambers hereof shown for example in FIGS. 5A, 5B, 6A, 6B, 7A, and 7B. The preferred embodiment, piezo-electric-type pressure transducers are molded into the walls of the expandable chambers 27.

In order that a health care professional using the apparatus of the present invention, can easily ascertain information regarding the surface-pressure and surface-temperature of the organ while compartmentalized by the flexible compartment defining structure hereof, the apparatus shown in FIG. 9 further includes a three dimensional (3D) organ modelling means 60, a visual display 65, and a keyboard/control means, connected in a manner known in the computer-graphic modelling art. The 3-D organ modelling means 65 is provided for generating a computer-generated model of the organ and providing the same in real-time to the visual display means 65 for visually displaying (i) a modelled organ, (ii) detected organ surface-temperatures, and (iii) surface-pressures shedded blood flow rates.

In the preferred embodiment, the 3D organ modelling means 60, visual display means 65, and keyboard/control means 70 is realized in the form of a 3D computer graphic work station 59 having 3D surface and solid modelling capabilities. Detected organ surface-temperature signals, organ surface-pressure signals and shedded blood flow rates, are provided to the 3D computer graphic work station 59 for are provided to the 3D computer graph display on respective portions of the 3D solid or surface model of the organ being modeled and visually displayed on a CRT display screen 65.

Thus, with the work station 59 a health professional can easily ascertain vital information regarding the state of a traumatized organ, and through the use of a user control/interface activatable through conventional keyboard 70 or other interface device of the work station 59, various organ surface-pressures and surface-temperatures can be programmably controlled and monitored in accordance with th principals of the present invention.

Referring now to FIGS. 1A, 1B, 1C, 2, 3 and 4, in particular, a present method of compartmentalizing an internal bodily organ of a patient which is massively bleeding, will now be described hereinbelow, in connection with the apparatus shown in FIGS. 5A and 5B.

Prior to compartmentalizing a massively bleeding liver in accordance with the present invention, the method of the present invention involves first mobilizing the liver in order to render a substantial portion thereto capable of being surrounded by the flexible-compartment defining structure shown for example, in FIGS. 5A/5B, FIGS. 6A/6B or FIGS. 7A/7B and described in great detail hereinabove.

Figure 1A:
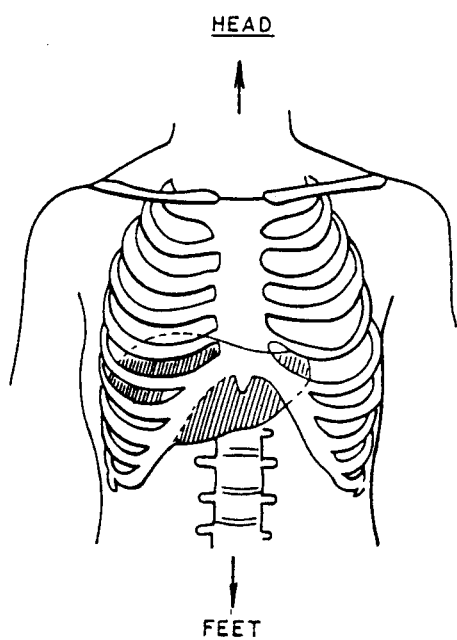
FIG. 1A is an anterior view of the human anatomy showing a portion of the skeletal system, the peritoneal cavity, and the liver situated therein.
Figure 1B:
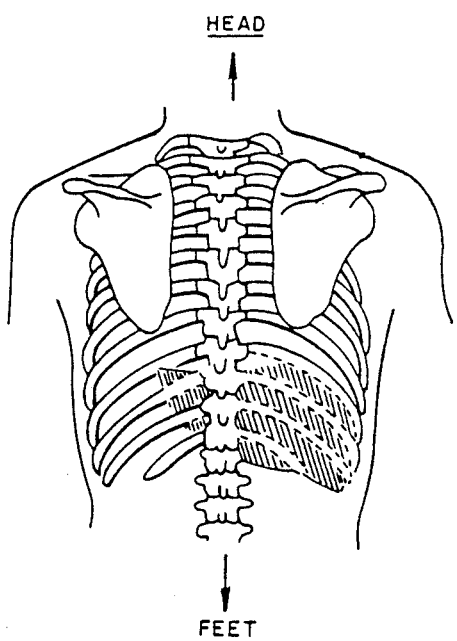
FIG. 1B is a posterior view of the human anatomy showing a portion of the skeletal system, the peritoneal cavity, and the liver situated therein.
Figure 1C:
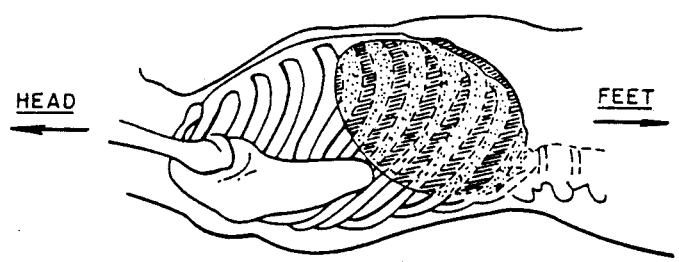
FIG. 1C is a side view of the human anatomy showing a portion of the skeletal system, the peritoneal cavity, and the liver situated therein.
Figure 2:
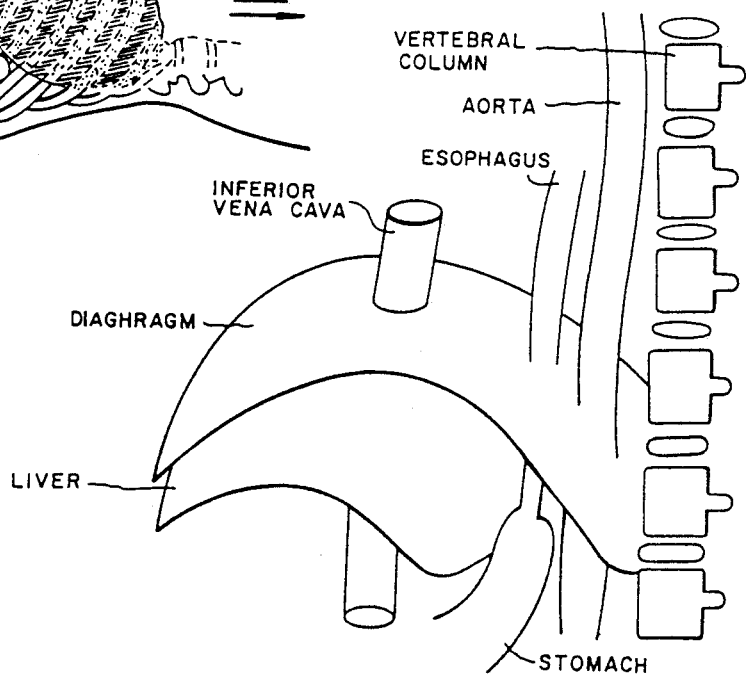
FIG. 2 is a side view of the liver as positioned below the diaphragm and in front of the esophagus, in the environment of the aorta Inferior vena cava and spinal column.
Figure 3:
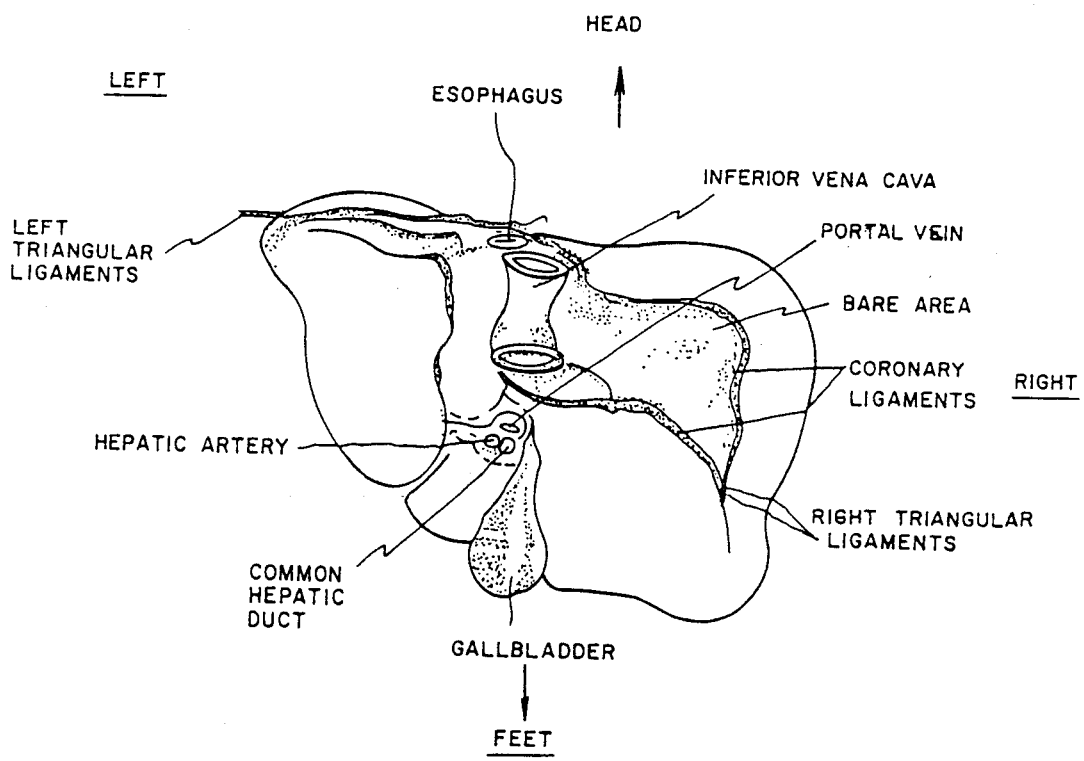
FIG. 3 is a posterior view of the liver showing the left and right triangular ligaments coronary ligaments and the falciform ligament which must be severed to partially detach the liver from the diaphragm, and other peritoneal structures.
Figure 4:
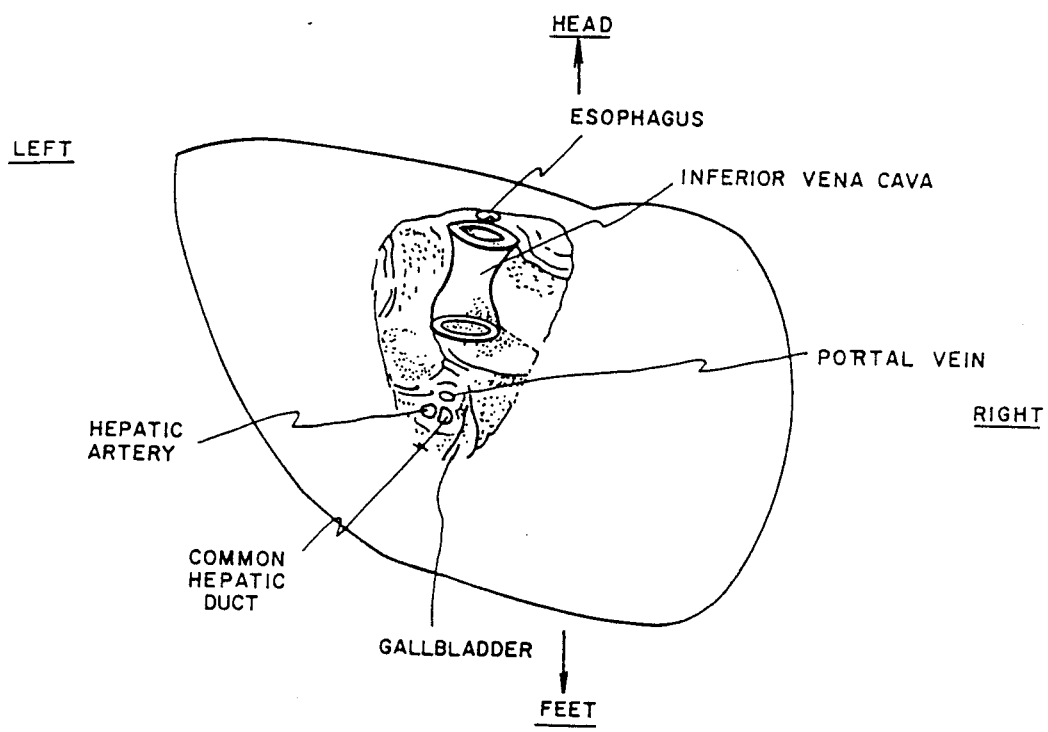
FIG. 4 is a posterior view of the liver shown in FIG. 3, with the compartment-defining apparatus of the present invention surrounding and compartmentalizing a substantial portion thereof, while vital anatomical structures, such as the inferior vena cava and "portal triad" (i.e. the bile duct, hepatic artery, and the portal vein) are disposed outside of the compartment-defining apparatus.

In general, FIGS. 1A, 1B and 1C show the position of the liver within the peritoneal cavity of a human patient. Notably, in FIG. 2, the liver is clearly shown to be below the diaphragm and as illustrated in FIG. 3, the left triangular ligament, right triangular ligament, coronary ligament and falciform ligament must be severed, so as to expose a major portion of the bare area of the diaphragm and freeing the liver from a large part of its attachments to the diaphragm and other peritoneal structures.

In a manner known to the medical profession, the relationship of the liver to the "portal triad", the gall bladder and inferior cava and hepatic veins will be left intact in their anatomical locations. Thus, by carrying such a procedure, a substantial portion of the liver will be mobilized and exposed without interfering with the vital functions of the liver and the remaining portions of the body.

After mobilizing the liver as described above, a substantial portion of the mobilized organ is surrounded with the flexible compartment-defining structure so as to compartmentalize a substantial portion thereof. Upon compartmentalizing the organ, the portal triad and inferior vena cava of the liver is allowed to project from the opening 5 formed in the flexible compartment-defining structure hereof, while the remaining surface area of the liver and the gall bladder is embraced by and compartmentalized within the flexible compartment-defining structure, akin to a jacket around the person's torso.

Upon compartmentalizing the liver, as described above, a volume of air or fluid is introduced into the input port 8 of the embodiment shown in FIGS. 5A/5B, for example, so as to cause the expandable receptacle means (i.e. expandable bladder or chamber 4) to inflate, expand and thereby apply a pressure distribution upon the external surface of the massively bleeding liver. This expansion can be achieved for example, by simply connecting a tube 71 and hand-held air bulb assembly 72 to input port 8 and squeezing the bulb to fill the expandable chamber 4 with air, or the more complicated pressure supply and control system 50 disclosed in FIG. 9, can be used as well. This volume-expansion effect of the expandable chamber 4, as described hereinbefore, applies pressure to the liver which, in turn, tamponades the bleeding. Also, shedded blood from the massively bleeding liver is collectable within the blood-tight compartment-defining structure 1 and can be allowed to exit through the drainage port 9 for collection and processing by the autotransfusion apparatus 40, illustrated in FIG. 9 in particular.

In order to determine the amount of pressure required to achieve full hemostasis of a massively bleeding liver, a conventional in-line type pressure gauge can be inserted along tubing 71 as illustrated in FIG. 5B, in order to obtain a reliable measure of the amount of surface pressure being applied to the bleeding organ.

Having applied a flexible compartment-defining structure hereof to an organ of a patient, several possible options are available to the health professional regarding how the apparatus is to be disposed. In each case, however, the options available depend on the particular embodiment of the compartment-defining apparatus hereof utilized, as well as the clinical status of the patient.

For example, using the apparatus illustrated in FIGS. 5A, 5B and 5C, the flexible expandable chamber 4 having been pressurized with sufficient volume of gas or liquid to achieve hemostasis, can be sealed off, for example, by clamping or otherwise hermetically occluding the gas/liquid port 8, using mechanical occluding devices, valves or functionally equivalent means. Regarding tubing attached to shedded-blood drainage port 9, an opening in the anterior abdominal wall of a patient can be formed so as to allow the tubing to be connected to an autotransfusion means 40, as shown in FIG. 9, so as to allow for monitoring of shedded blood, processing thereof and subsequent reinfusion into the patient, as described hereinbefore.

In the embodiment shown in FIG. 5B, a tube 71 connected to gas/liquid port 8 can be allowed to pass through the opening in the anterior abdominal wall of patient, and using a pressure gauge or meter inserted, for example, in the line of tubing 71, the health professional can (from outside of the body) increase or decrease (i.e. manipulate) the surface pressure applied to the organ, as he or she deems necessary in view of clinical status of the patient and the monitored conditions of shedded blood being collected.

The compartment-defining jacket-like apparatus hereof would be left in place in the body with pressure manipulation set as needed. The apparatus is then removed by another surgical procedure upon the discretion of the health care providers.

In the embodiment shown in FIGS. 8A and 8B, the flexible fluid-containing receptacle means 27 can be used to maintain the surface-temperature of an organ, such as the liver, during a liver transplant, with the provision of the organ surface-temperature control system shown in FIG. 9, for example Notably, with the to-be transferred liver compartmentalized within the flexible compartment-defining structure 1''' the surface temperature of the liver can be controlled in a required manner known in liver transplantation art. Preferably, the nature of the liquid or gas to be passed through the flexible tubular network 27, should have physical properties sufficient to achieve cooling, while not being toxic to the patient in the event of inadvertent leakage as by accident.

Having described hereinabove the various aspects of the present invention with respect to the liver, several alternative embodiments of the present invention come to mind with respect to application of the present invention to other organs are now apparent.

Figure 10A:
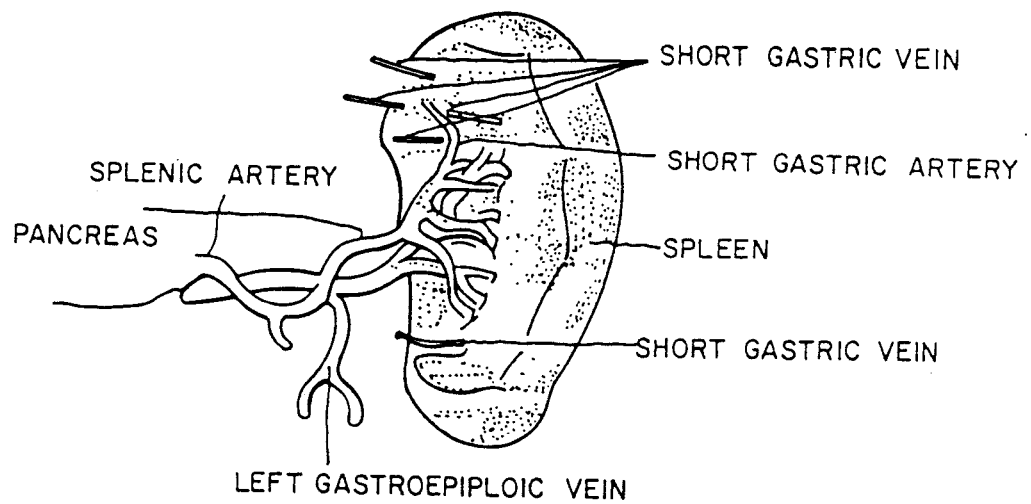
FIG. 10A is a view of the spleen shown after being mobilized by incising its anatomical attachments to the peritoneum, kidney, stomach, colon and greater omentum, leaving the splenic hilar structures (i.e. splenic artery and vein and tail of the pancreas) undisturbed.
Figure 10B:
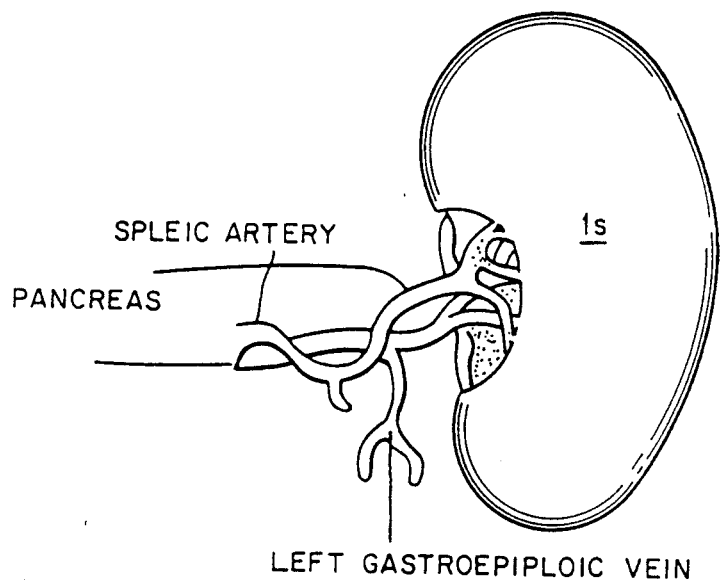
FIG. 10B is a perspective view of the spleen shown in FIG. 10A, with the embodiment of the compartment-defining apparatus hereof adapted for the spleen, surrounding and compartmentalizing a substantial portion thereof while vital anatomical structures, such as the splenic artery and vein and pancreas, are disposed outside of the compartment-defining apparatus.
Figure 11A:
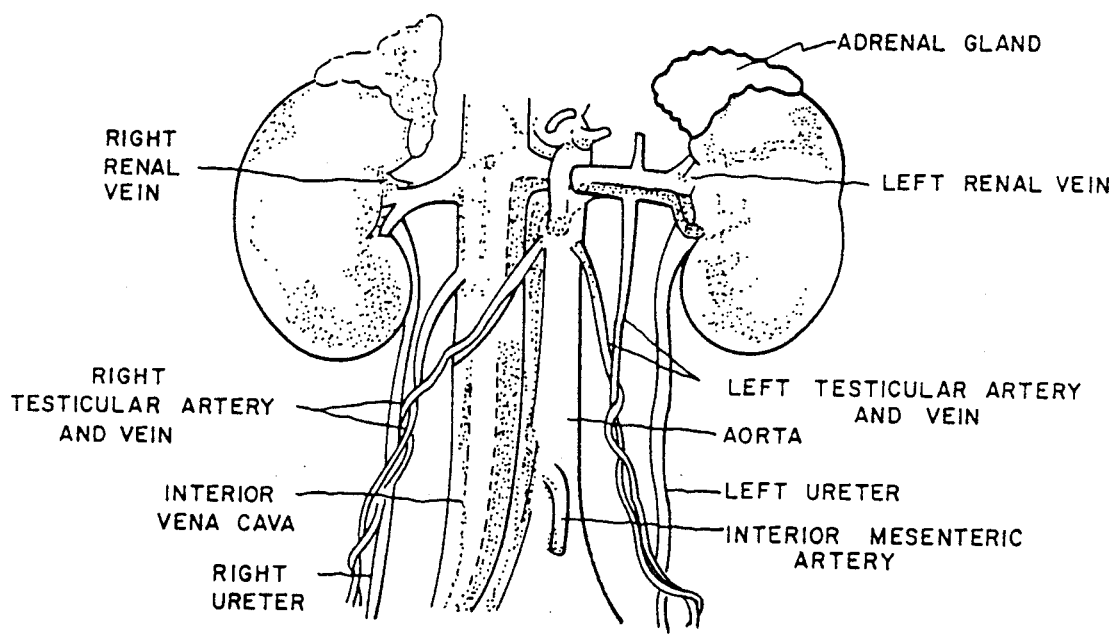
FIG. 11A is an anterior view of the kidneys shown after being mobilized by incising the overlying peritoneal attachments and Gerota's Fascia, leaving the renal hilum (i.e. renal artery and vein and renal pelvis) undisturbed.
Figure 11B:
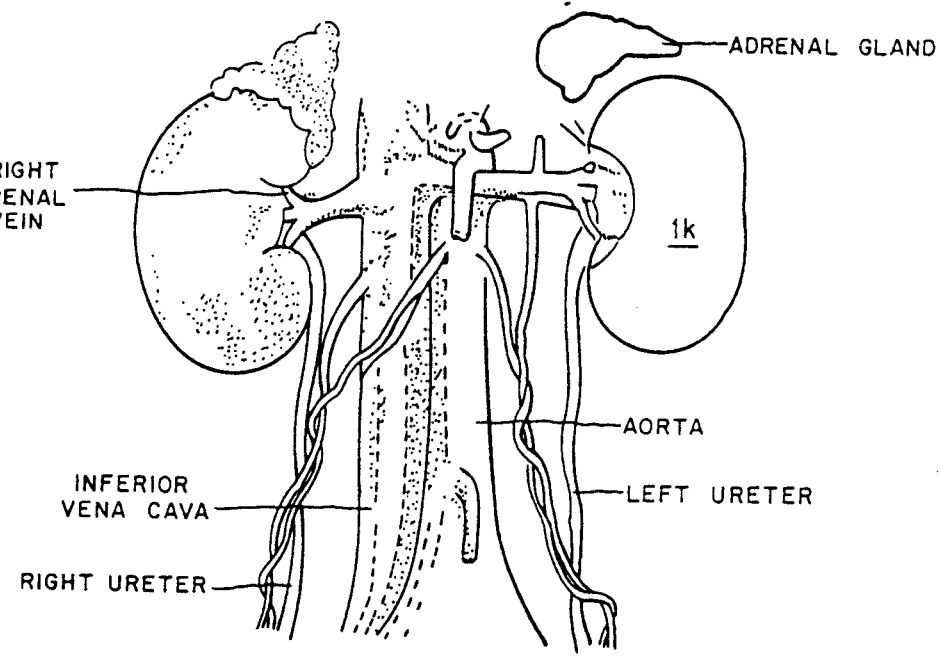
FIG. 11B is an anterior view of the kidneys shown in FIG. 11A, with the embodiment of the compartment-defining apparatus hereof adapted for a kidney, surrounding and compartmentalizing a substantial portion thereof, while vital anatomical structures of the organ, such as renal artery and vein and renal pelvis and ureter, are disposed outside of the compartment-defining apparatus.
Figure 12A:
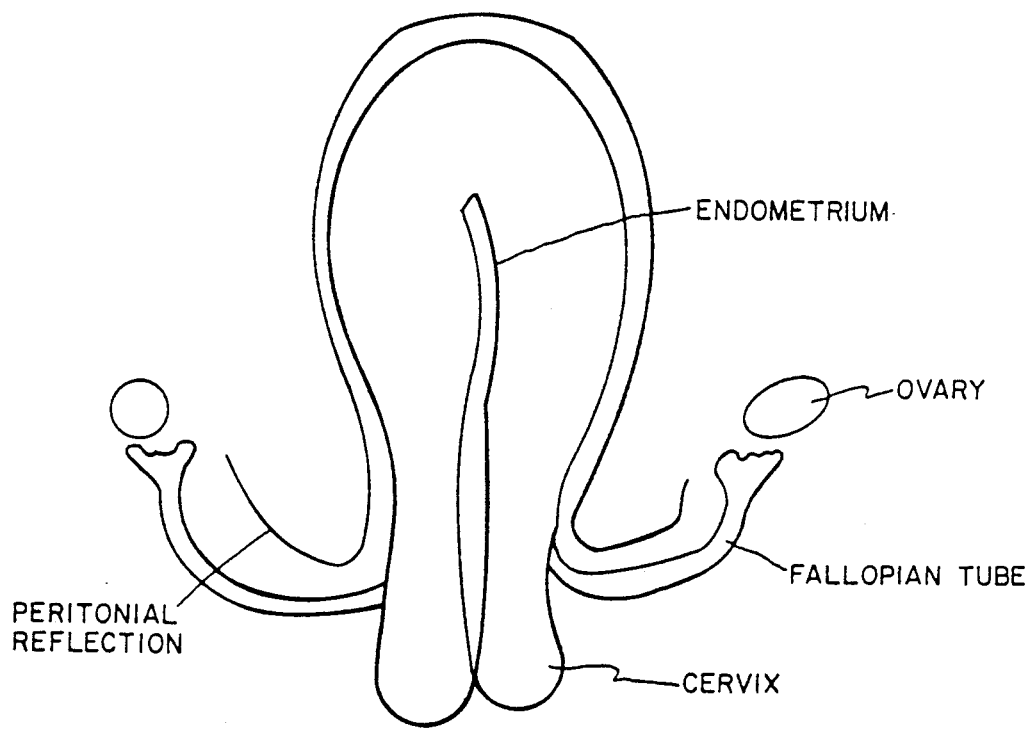
FIG. 12A is a graphical representation of a cross-section of the uterus showing the peritonealized portion thereof, fallopian tubes, ovaries and cervix.
Figure 12B:
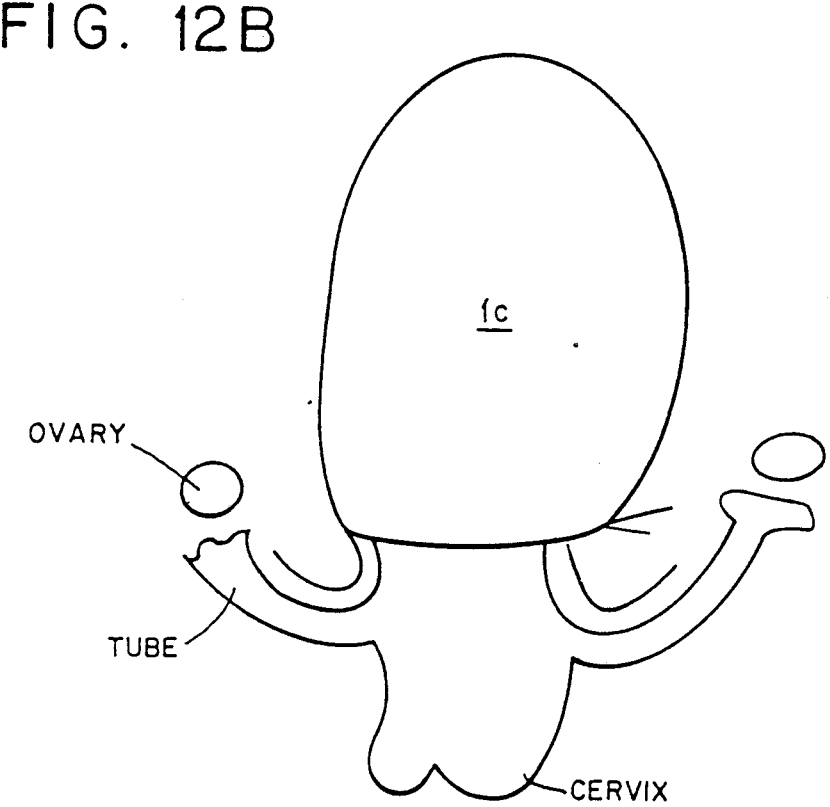
FIG. 12B is a graphical representation of the uterus shown in FIG. 12A, with the embodiment of the compartment-defining apparatus hereof adapted for the uterus, surrounding and compartmentalizing a substantial portion thereof, leaving the fallopian tubes, ovaries and cervix disposed outside of the compartment-defining apparatus.

For example, referring to FIGS. 10A, 10B, 11A, 11B, 12A and 12B in particular, the compartment-defining apparatus of the present invention is shown adapted for application to the spleen, kidney, and uterus, respectively. In each such embodiment, the physical dimensions of the flexible compartment-defining structure 1, are tailored so as to generally conform to the gross geometry of a substantial portion of the respective organ. As with the embodiments described with respect to the liver, the flexible compartment-defining structure for the spleen, kidney and uterus have also an inner surface and an outer surface, and is configurable so as to surround and compartmentalize a substantial portion of the spleen, kidney, and uterus, as illustrated in FIGS. 10B, 11B, and 12B, respectively.

However, in applying each of the organ-adapted compartment-defining apparatus illustrated in FIGS. 10B, 11B, and 12B, each organ requires that different surgical organ-mobilization procedures be carried out prior to the application of the compartment-defining apparatus hereof to its respective organ.

For example, the spleen can be mobilized by incising its anatomical attachments to the peritoneum, diaphragm, kidney, greater omentum, colon and stomach using a technique known in the surgical arts. After mobilization, the spleen is detached from the body except for its medial attachment to the splenic pedicle (i.e. artery and vein) and to the pancreas, thus rendering a substantial portion thereof capable of being surrounded by the flexible compartment-defining structure shown for example, in FIG. 10B.

In a similar fashion, a traumatized bleeding kidney would be mobilized by incising the surrounding peritoneum and Gerota's Fascia, thus detaching it from the posterior abdominal wall and adrenal gland, leaving its anatomical attachment to the renal artery, vein, pelvis and ureter intact, and thus rendering a substantial portion thereof capable of being surrounded by the flexible compartment-defining structure, shown, for example, in FIG. 11B.

In a similar fashion, the method and apparatus of the present invention may be applied to a uterus which is internally bleeding due to post partum, post-operative or other pathological processes, and not responding to conventional therapy. In this particular embodiment, the uterus is mobilized by retracting the uterus anteriorly and severing any attachments to the sigmoid, colon, urinary bladder, without intervening with the blood supply to the organ, or the attachments of the fallopian tubes, thus rendering the peritoneal portion of the uterus capable of being surrounded by and compartmentalized within the flexible compartment-defining structure as illustrated, for example, in FIG. 12B.

While the particular embodiments shown and described above are useful in many applications involving the surgical arts, further modification of the present invention herein disclosed will occur to those skilled in the art to which the present invention pertains and all such modifications are deemed within the scope and spirit of the present invention defined by the following claims.

What is claimed is:

1. An apparatus for compartmentalizing a substantial portion of a bleeding internal body organ of a patient, said apparatus comprising:
    a flexible compartment-defining structure having an inner surface and an outer surface, and having physical dimensions conforming to the gross geometry of said substantial portion of said organ;
    said inner surface of said flexible compartment-defining structure facing said organ; and
    a flexible expandable receptable means disposed over a substantial portion of said inner surface of said flexible compartment-defining structure and capable of containing a volume of gas or liquid for applying a distribution of pressure to said open to affect hemostasis thereon.

2. The apparatus of claim 1, wherein said flexible compartment-defining structure is made of a material which is impervious to blood.

3. The apparatus of claim 2, wherein said material is a substantially non-stretchable and gas/liquid non-permeable material.

4. The apparatus of claim 2, wherein said flexible compartment-defining structure further comprises a drainage port formed therein.

5. The apparatus of claim 4, wherein said port further comprises a connection means for connecting a tube having a first end and a second end to said port.

6. The apparatus of claim 5, which further comprises an auto transfusion means to which said tube is connected on said first end thereof and the second end of said tube is connected to said port receiving the shedded blood of said bleeding organ within said compartment. said auto transfusion means including a blood collection means for collecting and storing the blood received from said tube and a blood processing means for receiving the blood from said blood collection means and for processing said blood for reintroduction into said patient.

7. The apparatus of claim 1, wherein said flexible compartment-defining structure comprises:
    an outer flexible layer made of a substantially non-elastic material impervious to gas or liquid, and having physical dimensions sufficient to generally conform to the gross geometry of said substantial portion of said organ, and said outer flexible layer having a perimeter portion, and
    an inner flexible layer made of a material impervious to gas or liquid, and having physical dimensions sufficient to generally conform to the gross gemoetry of said substantial portion of said organ and said inner flexible layer having a perimeter portion, said inner flexible layer being hermetically sealed to said outer flexible layer so as to form said flexible expandable receptacle means, and said inner flexible layer forming said inner surface of said flexible compartment-defining structure and said outer flexible layer forming said outer surface of said flexible compartment-defining structure.

8. The apparatus of claim 7, wherein said inner flexible layer and said outer flexible layer are hermetically sealed with a patterned configuration so as to form said flexible expandable receptacle means.

9. The apparatus of claim 8, wherein said patterned configuration comprises a plurality of spaced apart circles enclosed by a perimeter boundary so as to thereby form a chamber between a substantial portion of said inner flexible layer and said outer flexible layer, said chamber capable of being filled with a volume of a gas or liquid.

10. The apparatus of claim 9, wherein said chamber is disposed over a substantial portion of said inner surface of said flexible compartment-defining structure and capable of containing a volume of gas or liquid for applying a pressure to said organ while said substantial portion of said organ is surrounded by and compartmentalized in said flexible compartment-defining structure generally conforming to the gross geometry of said organ.

11. The apparatus of claim 7, which further comprises:
   a sealing means for sealing said perimeter portions of said hermetically sealed inner flexible layer and said outer flexible layer, when said flexible compartment-defining structure is configured to surround and compartmentalize said substantial portion of said organ.

12. The apparatus of claim 1, wherein said flexible compartment-defining structure has physical dimensions sufficient to generally conform to the gross geometry of a substantial portion of an organ selected from the group consisting of the liver, the spleen, the uterus and the kidney.

13. The apparatus of claim 1, which further comprises a sealing means for bringing together and sealing said flexible compartment-defining structure, when configured to surround and compartmentalize said substantial portion of said organ.

14. The apparatus of claim 13 which further comprises
   a supply of gas or liquid having a pressure and in fluid communication with said flexible expandable receptacle means, said supply capable of illing said flexible expandable receptacle means with said gas or liquid so as to cause said flexible expandable receptacle means to expand while said flexible compartment-defining structure is configured to surround and compartmentalize said substantial portion of said organ, and thereby apply said pressure to said organ.

15. The apparatus of claim 14, which further comprises:
   at least one surface sensing means disposed on said inner surface of said flexible compartment-defining structure, for sensing pressure being applied by said gas or liquid in said flexible expandable receptacle means to the surface of said organ,
   register means for registering a predetermined surface-pressure value of said organ,
   control means for controlling the pressure of said supply of gas or liquid, in response to a pressure-adjustment signal, and
   comparing means for comparing said sensed surface-pressure with said predetermined surface-pressure value and producing a pressure adjustment signal in response to said comparison.

16. The apparatus of claim 15, which further comprises
   a plurality of surface-pressure sensing means disposed at spaced-apart locations on said inner surface of said compartment-defining structure, for sensing pressures along said organ surface and providing values therefor and
   display means for displaying the sensed organ surface pressure values.

17. The apparatus of claim 16, which further comprsies
   3-D organ modelling means for modelling said organ, and for providing said sensed surface-pressure values of said organ, and
   wherein said display means comprises a visual display means for displaying said modelling of said organ along with said sensed organ surface-pressure values.

18. The apparatus of claim 1, which further comprises a flexible fluid-containable receptacle means disposed over a substantial portion of said flexible compartment-defining structure, and capable of containing a fluid or gas, to be passed therethrough.

19. The apparatus of claim 18, which further comprises
   a supply of liquid or gas in fluid communicati-on with said flexible fluid-containable receptacle means,
   circulation means for circulating said liquid or gas through said flexible fluid-containable receptacle means, and
   temperature control means for controlling the temperature of said fluid or gas being circulated through said flexible fluid-containable receptacle means.

20. The apparatus of claim 19, which further comprises
   a plurality of surface-temperature sensing means disposed on said flexible compartment-defining structure for sensing the surface-temperature or said organ surrounded by and compartmentalized with said flexible compartment-defining structure, and
   wherein said temperature-control means is capable of programming controlling the temperature of said gas or liquid in response to said sensed surface-temperature of said organ by said surface-temperature sensing means.

21. The apparatus of claim 19, which further comprises
   a monitoring means for monitoring sensed surface-temperature of said organ, and for displaying said surface-temperatures on a display means.

22. An apparatus for surrounding a bleeding internal body organ, and arrest said organ bleeding, said apparatus comprising:
   an outer flexible layer made of a substantially non-elastic material impervious to gas or liquid, and having physical dimensions sufficient to generally conform to the gross geometry of the internal bodily organ and said outer flexible layer having a perimeter edge,
   an inner flexible layer made of a material impervious to gas or liquid, and having physical dimensions sufficient to generally conform to the gross geometry of the internal bodily organ and said inner flexible layer having a perimeter edge,
   said inner flexible layer being positioned around said outer flexible layer and hermetically sealed thereto at the perimeter edges of said inner flexible layer and said outer flexible layer to form a jacket-like assembly having a hermetically sealed chamber between said outer flexible layer and said inner flexible layer, and a compartment substantially conforming to the gross geometry of said internal bodily organ, said chamber capable of being filled with a pressurized gas or liquid which causes said inner flexible layer to expand and distribute the pressure of said gas or liquid to said internal body organ to affect hemostasis thereon; and
   sealing means for maintaining said outer and said inner perimeter edges relatively fixed while said chamber is filled with said pressurized gas or liquid.

* * * * *